US008927545B2

(12) United States Patent
Qiao et al.

(10) Patent No.: US 8,927,545 B2
(45) Date of Patent: Jan. 6, 2015

(54) INHIBITING EPH B-3 KINASE

(75) Inventors: Lixin Qiao, Tewksbury, MA (US); Marcie Glicksman, Winchester, MA (US); Thomas Gainer, Swampscott, MA (US); Donald C. Lo, Chapel Hill, NC (US); Ross L. Stein, Cambridge, MA (US); Sungwoon Choi, Sharon, MA (US); Gregory D. Cuny, Somerville, MA (US)

(73) Assignees: Duke University, Durham, NC (US); The Brigham and Women's Hospital, Inc., Boston, MA (US)

( * ) Notice: Subject to any disclaimer, the term of this patent is extended or adjusted under 35 U.S.C. 154(b) by 446 days.

(21) Appl. No.: 13/260,990

(22) PCT Filed: Mar. 30, 2010

(86) PCT No.: PCT/US2010/029209
§ 371 (c)(1),
(2), (4) Date: May 23, 2012

(87) PCT Pub. No.: WO2010/117787
PCT Pub. Date: Oct. 14, 2010

(65) Prior Publication Data
US 2012/0238597 A1 Sep. 20, 2012

Related U.S. Application Data

(60) Provisional application No. 61/164,670, filed on Mar. 30, 2009.

(51) Int. Cl.
| | | |
|---|---|---|
| *A61K 31/535* | (2006.01) | |
| *C07D 491/02* | (2006.01) | |
| *C07D 498/02* | (2006.01) | |
| *C07D 513/02* | (2006.01) | |
| *C07D 515/02* | (2006.01) | |
| *A61K 31/437* | (2006.01) | |
| *A61K 31/00* | (2006.01) | |

(52) U.S. Cl.
CPC ............... *A61K 31/437* (2013.01); *A61K 31/00* (2013.01)
USPC .......................... 514/234.2; 514/300; 546/121

(58) Field of Classification Search
USPC ................. 514/300, 234.2; 546/121
See application file for complete search history.

(56) References Cited

U.S. PATENT DOCUMENTS 4,492,695 A * 1/1985 Kaplan et al. ............ 514/210.18

FOREIGN PATENT DOCUMENTS

| WO | WO 01/45638 | 6/2001 |
|---|---|---|
| WO | WO 02/099117 | 12/2002 |
| WO | WO 2005/012298 | 2/2005 |
| WO | WO 2008/009487 | 1/2008 |

OTHER PUBLICATIONS

Georgescu et al. Revue Romaine de Chimie, 2005, vol. 50, Issue 5, Abstract.*
Georgescu, et al. Revue Roumaine de Chimie, 2005, vol. 50, Issue 5, pp. 349-352.*
International Search Report and Written Opinion in International Application No. PCT/US2010/029209, mailed Jan. 25, 2011, 10 pages.
International Preliminary Report on Patentability in International Application No. PCT/US2010/029209, mailed Oct. 13, 2011, 6 pages.
Albers et al., "Safety, Tolerability, and Pharmacokinetics of the N-Methyl-D-Aspartate Antagonist Dextrorphan in Patients with Acute Stroke," *Stroke*, 1995, 26:254-258.
Aoto and Chen, "Bidirectional ephrin/Eph signaling in synaptic functions," *Brain Res.*, Dec. 2007, 1184:72-80.
Bembenek et al., "Characterization of the Kinase Domain of Ephrin-B3 Receptor Kinase Using a Scintillation Proximity Assay," *Assay Drug Develop. Technol.*, 2003, 1:555-563.
Coppola and Damon, "Acetylenic Amides. I. Synthesis of N-Substituted-2-propynamides," *Syn. Comm.*, 1993, 23:2003-2010.
GenBank Accession No. NM 004443, 1993, 6 pages.
Himanen et al., "Cell-cell signaling via Eph receptors and ephrins," *Curro Opin. Cell Biol.*, 2007, 19:534-542.
Holder et al., "Mini-Review: The Eph receptor tyrosine kinases and the ephrins—roles in nervous system development," *Eur. J Neurosci.*, 1998, 10:405.
Kullander and Klein, "Mechanisms and Functions of Eph and Ephrin Signaling," *Nature Rev. Mol. Cell Biol.*, 2002, 3:475-486.
Lipinski et al., "Experimental and computational approaches to estimate solubility and permeability in drug discovery and development settings," *Adv Drug Del Rev.*, 1997, 23:3-25.
Liu et al., "EphB3: An Endogenous Mediator of Adult Axonal Plasticity and Regrowth after CNS Injury," *J Neurosci.*, 2006, 26:3087-3101.
Lo et al., "Neuronal Transfection in Brain Slices Using Particle-Mediated Gene Transfer," *Neuron*, 1994, 13:1263-1268.
Lo, "Neuronal transfection using particle-mediated gene transfer," *Curr Protoc Neurosci*, 2001, 3.15, 14 pages.
Marler and Goldstein, "Medicine. Stroke-tPA and the clinic," *Science*, 2003, 301(5640):1677.
McBride et al., "The hexaphenylethane riddle," *Tetrahedron*, 1974, 30:2009-2022.
Miranda et al., "Induction of Eph B3 after Spinal Cord injury," *Exp. Neural.*, 1999, 156:218-222.

(Continued)

*Primary Examiner* — Samira Jean-Louis
(74) *Attorney, Agent, or Firm* — Fish & Richardson P.C.

(57) ABSTRACT

EphB3 kinase inhibitor compounds, including certain pyrazolo[1,5-a]pyridine and imidazo[1,2-a]pyridine compounds, inhibit EphB3 kinase. The EphB3 kinase inhibitor compounds can have greater potency for the inhibition of EphB3 kinase than general kinase inhibitors. Pharmaceutical compositions, such as neuroprotective agents, comprising the EphB3 kinase inhibitor compounds are also provided. The EphB3 kinase inhibitor compounds and pharmaceutical compositions are useful, for example, to provide neuroprotection and/or repair of neuronal tissue damaged during an ischemic event, such as a stroke.

15 Claims, 19 Drawing Sheets

(56) References Cited

OTHER PUBLICATIONS

Pasquale, "Eph receptor signaling casts a wide net on cell behavior," *Nature*, 2005, 6:462-475.

Pasquale, "Eph-Ephrin Bidirectional Signaling in Physiology and Disease," *Cell*, 2008, 133:38-52.

Schurr and Rigor, Emerging Strategies in Neuroprotection. Birkhauser, Boston, 1992, 2:24-43.

Strausberg et al., "The Mammalian Gene Collection," *Science*, 1999, 286:455-457.

Takasu et al., "Modulation of NMDA Receptor Dependent Calcium Influx and Gene Expression Through EphB Receptors," *Science*, 2002, 295:491-495.

Tamura et al., "Effects of 3-Substituents upon Orientation in the 1,3-Dipolar Cyclo-addition Reaction Between 3-Substituted Pyridine $N$-Imides and Ethyl Propiolate: Syntheses of Ethyl 4- and 6-substituted Pyrazolo[1,5-α]- pyridine-3-carboxylates," *J Chem. Soc., Perkin Trans. 1*, 1975, 406-409.

Tamura et al., "Synthesis of a chiral molecular square with two organic corners," *Tetrahedron Lett.*, 1999, 40:4133-4136.

Wang et al., "Cardiac Glycosides Provide Neuroprotection Against Ischemic Stroke: Discovery by a Brain Slice-Based Compound Screening Platform," *PNAS*, 2006, 103:10461-10466.

Willson et al., "EphB3 receptor and ligand expression in the adult rat brain," *J Mol. Hist.*, 2006, 37:369-380.

Willson et al., "Transection of the Adult Rat Spinal Cord Upregulates EphB3 Receptor and Ligand Expression," *Cell Transplant*, 2003, 12:279-290.

Yang et al., "Prevention of apoptosis by Bcl-2: release of cytochrome c from mitochondria blocked," *Science*, 1997, 275:1129-32.

Zhang et al., "A simple statistical parameter for use in evaluation and validation of high throughput screening assays," *J Biomol Screen*, 1999, 4:67-73.

\* cited by examiner

INHIBITING EPH B-3 KINASE

CLAIM OF PRIORITY

This application is a 371 National Stage Application of International Application No. PCT/US2010/029209, filed Mar. 30, 2010, which claims the benefit of priority of U.S. Provisional Application No. 61/164,670, filed Mar. 30, 2009, each of which is incorporated herein by reference in its entirety.

STATEMENT OF GOVERNMENT FUNDING

This invention was made with funding under National Institutes of Health grant No. NS049339. The Government has certain rights in the invention.

TECHNICAL FIELD

This disclosure relates to modulating kinase activity of the erythropoietin-producing hepatocellular carcinoma (Eph) B3 receptor.

BACKGROUND

Erythropoietin-producing hepatocellular carcinoma (Eph) receptors are highly conserved transmembrane proteins composed of multiple domains that participate in an array of complex cell signaling pathways. Vertebrates have sixteen Eph receptors, divided into two major classes, EphA (EphA1-EphA10) and EphB (EphB1-EphB6) based on sequence similarity in the extracellular domain and binding characteristics.

The Eph receptors interact with cell surface ligands called Eph receptor interacting proteins (ephrins). Currently, nine ephrins are known and are divided into two major classes (ephrin A1-6 and ephrin B1-3). Following binding of the Eph receptors and the ephrin ligands, which requires cell-cell interactions, propagation of signaling occurs bi-directionally into both the Eph receptor and the ephrin presenting cells. The signaling events resulting from these interactions are important in both neural development and during adulthood. For example, the Eph receptors together with ephrins participate in axon guidance by providing repulsive cues during axonal neurogenesis.

The EphB3 receptor subtype is expressed during embryonic development and in discrete areas of the adult brain, including the cerebellum and hippocampus. It co-localizes to brain regions with high levels of ephrin B ligand expression. EphB3 receptor expression also increases following central nervous system injury.

SUMMARY

This disclosure relates to EphB3 kinase inhibitors, including compounds that inhibit EphB3 kinase activity. The invention is based on the discovery of chemical compounds that inhibit the activity of EphB3 tyrosine kinase enzyme, including Eph B3 kinase inhibitor compounds that inhibit EphB3 phosphorylation by an EphB3 kinase of the BTK-peptide (SEQ ID NO:4) with an IC50 of about 20 micromolar or less. The EphB3 kinase can be a full length recombinant human EphB3 kinase enzyme (e.g., SEQ ID NO:1) or a truncated recombinant human EphB3 kinase (e.g., SEQ ID NO: 2 or SEQ ID NO:3) that phosphorylates a BTK peptide (SEQ ID NO:4) in the absence of the Eph B3 kinase inhibitor compound.

In particular, the disclosure provides EphB3 kinase inhibitor compounds, including pyrazolo[1,5-a]pyridine and imidazo[1,2-a]pyridine compounds. Examples of the pyrazolo[1,5-a]pyridine EphB3 kinase inhibitor compounds include compounds of Formula (Ia):

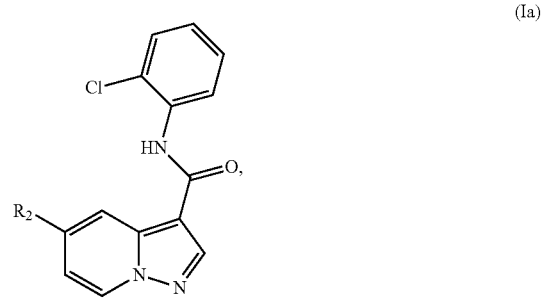

(Ia)

wherein $R_2$ is selected from the group consisting of hydrogen, halogen, lower ($C_1$-$C_8$) alkyl (e.g., methyl), alkoxy (e.g., methoxy), amino, aminoalkyl (e.g., dimethylamino), cycloalkyl, cycloheteroalkyl (e.g., pyrrolidinyl, piperidinyl, morpholinyl, and the like), aryl (e.g., phenyl), and oxyaryl (e.g., oxybenzyl). Examples of the imidazo[1,2-a]pyridine EphB3 kinase inhibitor compounds include compounds of Formula (IIa):

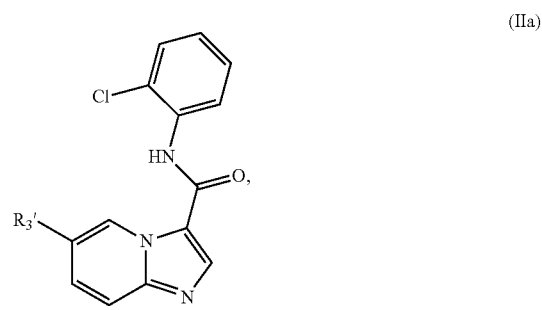

(IIa)

wherein $R_3'$ is selected from the group consisting of hydrogen, halogen, cycloalkyl, cycloheteroalkyl (e.g., piperidinyl, piperidinolyl, and the like), and aryl (e.g., phenyl). The EphB3 kinase inhibitor compounds can have greater potency for the inhibition of EphB3 kinase than general kinase inhibitors, such as staurosporine and PP2. Pharmaceutical compositions, such as neuroprotective agents, comprising the EphB3 kinase inhibitor compounds are also provided.

In another aspect, the disclosure provides methods for the use of EphB3 kinase inhibitor compounds for treating a medical condition associated with erythropoietin-producing hepatocellular carcinoma receptor B3, such as an EphB3 kinase-mediated medical condition. For example, methods of providing neuroprotection and/or treatment for neural tissue damaged after ischemic neural events are also provided. The EphB3 kinase inhibitor compounds can be used in combination with, or as an alternative to, administration of compounds to protect against neuronal cell death (e.g., MK-801 and/or dextrorphan). The EphB3 kinase inhibitor compounds are believed to be particularly useful in mitigating or preventing the neuronal tissue damage resulting from ischemic events such as cerebral ischemia, traumatic brain injury and other neurodegenerative conditions.

DESCRIPTION OF DRAWINGS

As shown in FIG. 2A, addition of 1.875 mM DTT to a 15 mM Hepes, pH 7.5, buffer containing 1% glycerol, 0.01% Tween, and 1% DMSO, stabilized the enzyme for at least 1 hr at RT. FIG. 2B shows BTK phosphorylation by EphB3 was dependent on $MnCl_2$ when compared to $MgCl_2$. FIG. 2C shows that EphB3 was tolerant of DMSO concentrations <4% without much loss of activity. FIG. 2D shows that EphB3 enzyme activity under optimized conditions was unaffected by a freeze/thaw cycle and showed no variation in activity between the two available enzyme lots when tested for up to 90 min. All error bars represent the standard deviation of 3 replicate wells per condition.

FIG. 3 shows the rate of BTK phosphorylation by EphB3 kinase at 3.13, 6.25, and 12.5 nM as a function of the change in the dF (ratio of the two signals) over time. Under saturating conditions, 6 µM substrate and 25 µM ATP concentrations, BTK substrate was phosphorylated in a linear time-dependent fashion for up to 1 hr at all enzyme concentrations. Error bars represent the standard deviation of 3 replicate wells per condition.

In FIG. 4A, BTK substrate phosphorylation by 12.5 nM EphB3 kinase is shown at saturating ATP concentration (25 µM). $V_{max}$ was determined to be about 0.3 nM/min and $K_m$ was about 600 nM. In FIG. 4B, BTK substrate phosphorylation by 12.5 nM EphB3 is shown at ATP concentrations from 0.78 to 25 µM. At 6 µM saturating substrate condition, $V_{max}$ for ATP was determined to be about 0.3 nM/min and $K_m$ was about 2.0 µM. Error bars represent the standard deviation of 3 replicate wells per condition.

As shown in FIG. 5A, Staurosporine weakly inhibited activity with 50% inhibition at 100 µM, which was the highest concentration that could be tested. As shown in FIG. 5B, PP2 inhibited activity completely and the IC50 value was determined to be 1.7+0.6 µM. Error bars represent the standard deviation of 3 replicates per condition.

DETAILED DESCRIPTION

Figure 1:
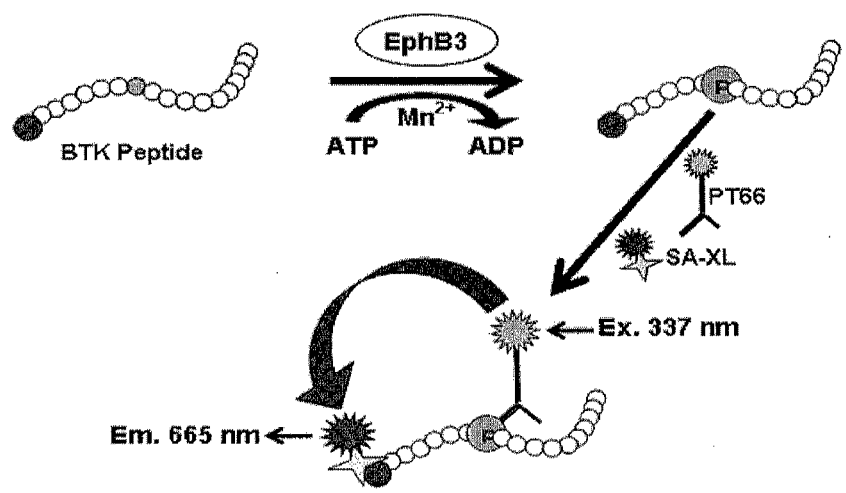
FIG. 1 is a schematic representation of the HTRF assay designed to measure the phosphorylation of BTK substrate by EphB3 kinase is shown.
Figure 2A:
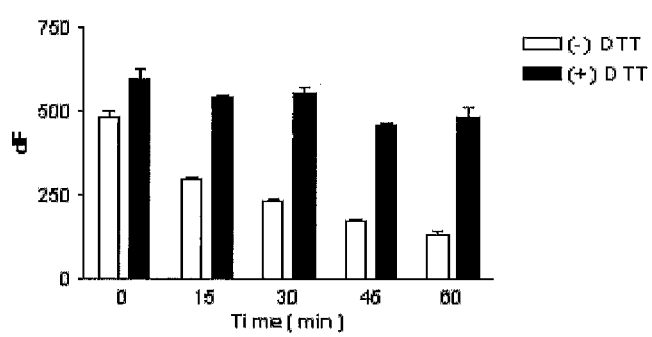
FIGS. 2A-2D are graphs showing the Delta F (dF) (i.e., the ratio of the difference between the sample and negative control 665/620 ratios to the difference between the negative control ratio) as a function of time used to optimize the BTK phosphorylation activity by EphB3.
Figure 2B:
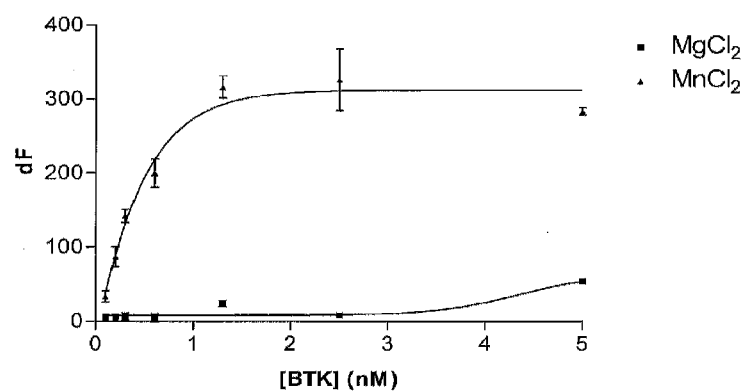
Figure 2C:
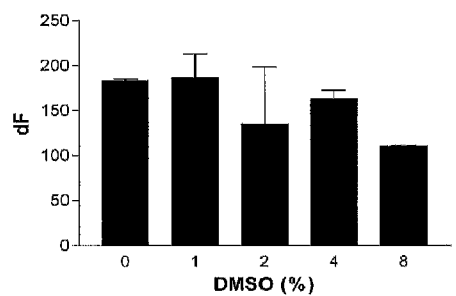
Figure 2D:
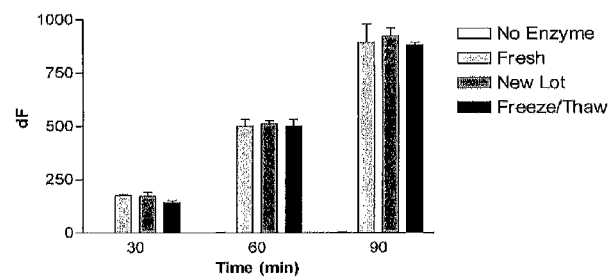

This disclosure describes methods of identifying EphB3 kinase inhibitor compounds, compounds that inhibit EphB3 kinase, pharmaceutical compositions including EphB3 kinase inhibitor compounds, and methods of using the EphB3 kinase inhibitor compounds. Preferably, the EphB3 kinase inhibitor compounds have greater potency for the inhibition of EphB3 kinase than general kinase inhibitors. The EphB3 kinase inhibitor compounds and pharmaceutical compositions are useful, for example, to provide neuroprotection and/or repair of neuronal tissue damaged during an ischemic event, such as a stroke.

Unless otherwise indicated, "EphB3 Kinase Inhibitor compounds" refer to compounds that inhibit EphB3 phosphorylation of the BTK-peptide (SEQ ID NO:4). For example, the EphB3 Kinase Inhibitor Compounds can have an IC50 for inhibiting EphB3 phosphorylation of the BTK peptide (SEQ ID NO:4) of about 20 micromolar or less according to the assay described herein (e.g., an IC50 value of less than 0.1 to about 20, less than 0.1 to about 15, less than 0.1 to about 15, less than 0.1 to about 2.0, less than 0.1 to about 1.0, less than 0.1 to about 0.3, less than 0.1 to about 0.2, less than about 0.1, less than about 0.2, less than 0.3, less than about 1.7 or less than about 0.8 micromolar).

Unless otherwise indicated, recitation of an "optionally substituted" chemical structure refers to the chemical structure with and without one or more chemical substituents chemically bound to an atom of the chemical structure. Examples of optional substituents include hydroxyl, halogen, and amine moieties.

In some embodiments, each alkyl group, used alone or in combination with another term, has 1 to 8 carbon atoms (e.g., $C_1$-$C_8$).

Unless otherwise indicated, recitation of "alkoxy" refers to a chemical moiety comprising an oxygen bound both as a substituent to another chemical structure and to a carbon atom (e.g., a group of formula —O-alkyl, such as a methoxy moiety).

Unless otherwise indicated, recitation of "aminoalkyl" refers a secondary or tertiary amine substituted with at least one alkyl group (e.g., methylamino, dimethylamino, and the like).

Unless otherwise indicated, recitation of "cycloalkyl" refers to a closed ring carbon structure of three or more carbon atoms. In some embodiments, the cycloalkyl group is a monocyclic ring of 3 to 7 carbon atoms.

Unless otherwise indicated, recitation of "cycloheteroalkyl" refers to optionally substituted non-aromatic closed ring chemical structures having carbon atoms and one or more non-carbon atoms (e.g., nitrogen, oxygen and sulfur). In some embodiments, the cycloheteroalkyl group is a monocyclic ring of 2 to 7 carbon atoms and having 1, 2, 3, or 4 heteroatoms independently selected from nitrogen, oxygen and sulfur.

Unless otherwise indicated, recitation of "aryl" refers to optionally substituted aromatic structures comprising one or more closed carbon ring chemical structures. In some embodiments, the aryl group is a naphthalene ring or a phenyl ring. In some embodiments, the aryl group is phenyl.

Unless otherwise indicated, recitation of "heteroaryl" refers to optionally substituted aromatic structures comprising one or more closed ring chemical structures having carbon atoms and one or more non-carbon atoms (e.g., nitrogen, oxygen and sulfur). In some embodiments, the heteroaryl group is a monocyclic aromatic ring of 1 to 7 carbon atoms and having 1, 2, 3, or 4 heteroatoms independently selected from nitrogen, oxygen and sulfur.

Unless otherwise indicated, recitation of "alkylaryl" refers to optionally substituted aromatic structures joined to another chemical structure by an alkyl moiety (e.g., benzyl).

Unless otherwise indicated, recitation of "oxyaryl" refers to optionally substituted aromatic structures joined to another chemical structure by an oxygen (e.g., oxybenzyl).

Identifying EphB3 Kinase Inhibitor Compounds

EphB3 Kinase Inhibitor compounds were identified based on the ability of compounds to inhibit EphB3 phosphorylation of a BTK peptide by an EphB3 receptor tyrosine kinase. The EphB3 receptor tyrosine kinase used was either (1) a full length recombinant human EphB3 kinase (SEQ ID NO:1) enzyme (available as GenBank accession No. NM 004443) or (2) a truncated recombinant human EphB3 kinase (e.g., SEQ ID NO: 2 or SEQ ID NO:3) that phosphorylates a BTK peptide of SEQ ID NO:4 in the absence of the Eph B3 Kinase Inhibitor compound. The recombinant human EphB3 kinase of SEQ ID NO:1 can be produced using a baculovirus expression system with a construct expressing human EphB3 amino-terminally fused to a GST-6-Thrombin cleavage site and purified by 1-step affinity purification using glutathione-agarose. The recombinant human EphB3 kinase (SEQ ID NO:1) can also be purchased (e.g., Novus Biologicals, Littleton, Colo.). The EphB3 receptor tyrosine kinase of SEQ ID NO:1 is the full length kinase including an intact globular domain of EphB3 and a transmembrane domain. The truncated recombinant human EphB3 kinase (SEQ ID NO:2) can be obtained, for example, from Cell Signaling Technology, Danvers, Mass.) as catalog number 7749, a 414 amino acid N-terminal fragment, or the truncated recombinant human EphB3 kinase (SEQ ID NO:3) can be obtained from Invitrogen Corporation (Carlbad, Calif.) as catalog number PV4102, a 347 amino acid N-terminal fragment. The truncated forms do not include the transmembrane domain. BTK is a synthetic 17 amino acid sequence biotin-AGAGLKKVVALY*DYMPM (SEQ ID NO:4), where Y* is the site of phosphorylation.

The EphB3 receptor was identified as a neuroprotective drug target candidate in brain slice explants using particle-mediated gene transfer ("biolistics"). DNA expression constructs encoding two different fluorescent proteins (e.g., YFP-expression construct and CFP-expression construct) were delivered to cortical brain slice explants. Transient oxygen-glucose deprivation (OGD) was then applied to chronic cortical brain slice explants (See Wang et al., "Cardiac Glycosides Provide Neuroprotection Against Ischemic Stroke Discovery by a Brain Slice-Based Compound Screening Platform," Proc Natl Acad Sci USA 2006; 103:10461-10466). The DNA expression constructs thereby created a "sentinel" population of neurons with which the degenerative state of the brain slices post-ischemic injury could be monitored visually at the level of the morphology of individual cortical neurons. In this gene-based assay, two types of gold particles were mixed together before the biolistic transfection of cortical brain slice explants: 1) those co-coated with the YFP-expression construct and an individual cDNA from a cDNA library; and 2) those co-coated with a cyan fluorescent protein (CFP)-expression construct and the cloning vector backbone. Transfection densities were adjusted such that each neuron within brain slices never received more than one gold particle; thus, individual neurons transfected with YFP-gold or CFP-gold, but never both, were randomly dispersed and intermixed within each slice. The CFP-transfected neuronal population thereby served as an "in-slice" internal control and the neuroprotective potential of the cDNAs co-transfected into the YFP-expressing neurons could thus be compared directly with neighboring CFP-expressing neurons that received vector backbone only. Various candidate cDNA clones were assayed using this method. Positive hits were then re-prepped and re-assayed to exclude false-positives and to establish statistically significant rescue of transfected neurons in OGD brain slices relative to the internal CFP-expressing neuronal control population. A significantly neuroprotective cDNA clone encoding EphB3 sequences was identified using this method.

EphB3 kinase inhibitor compounds were identified using a low volume homogeneous assay, described in detail in Examples 1-6. The assay format utilized homogeneous time resolved fluorescence assay format (HTRF) where the phosphorylation of a tyrosine containing peptide substrate by recombinant EphB3 kinase domain was measured by the fluorescence resonance energy transfer (FRET) produced between the close proximity and interaction of a europium labeled anti-phosphotyrosine antibody and streptavidin-allophycocyanin acceptor (SA-XL665) bound to the biotinylated substrate (Example 1). The assay allowed control for signal interference from compounds and proteins that naturally fluoresce or absorb. Due to the long lived fluorescent signal of SA-XL665, the energy signal was determined following the decay of any natural fluorescent signals from the compounds. In addition, the 665 nm emission signal of the SA-XL665 was in the far red-shift of the light spectrum limiting the interference of small molecules in the fluorescent readout that commonly occur at lower wavelengths of light such as in the fluorescein range of 488 nm. Thus, the nature of the fluorophore pairs and biomolecules allowed specific measurement of substrate phosphorylation with minimal interference. The working enzyme concentration and enzyme velocity were determined according to Example 2, and substrate $V_{max}$ and $K_m$ values were determined for BTK (Example 3) and ATP (Example 4). The enzyme composition was optimized for enzyme stability (Example 5) and enzyme concentration (Example 6).

To perform the assay, candidate compounds were preincubated with the enzyme for 30 minute in a 6 microliter reaction volume. The reaction was stopped after 60 minutes which was in the linear range of the progress curve and at the $K_m$ for the substrates. Assay validation with multiple plates containing only control DMSO concentration was found to be robust with signal variation within plates and between plates less than 10% and Z'-factors greater than 0.7. Duplicate compound plates are also run as part of the validation to determine the initial hit rate, the concordance between the duplicate wells, and the behavior of the assay in the presence of compounds. Fresh lyophilized powder of each compound was obtained from the original vendor and 12-point dose response curves were generated to determine IC50 values for candidate compounds.

Figure 5A:
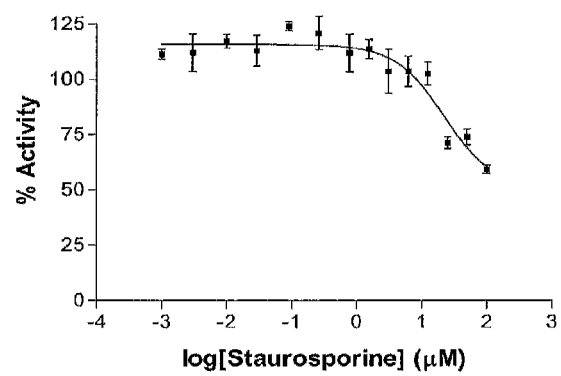
FIGS. 5A-5B relate to the determination of IC50 values of known kinase inhibitors. IC50 values for staurosporine (FIG. 5A) and PP2 (FIG. 5B) were determined by treating 12.5 nM EphB3 with compound for 30 min at RT in the presence of 2.5 µM ATP. Phosphorylation was then determined after the addition of 600 nM BTK for 1 hr.
Figure 5B:
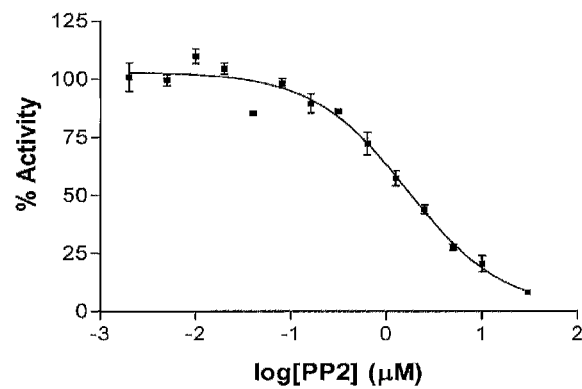

The assay was used to measure EphB3 tyrosine kinase inhibition for two known general kinase inhibitors, staurosporine and PP2 (src family kinase inhibitor). The results are shown in FIG. 5. Staurosporine weakly inhibited phosphorylation reaching 50% at the highest concentration tested, 100 μM. The inhibition was similar to the reported value by the manufacturer of the kinase (Cell Signaling Technology). PP2 inhibited phosphorylation more potently with an IC50 value of 1.7+0.6 μM. Published data on a scintillation proximity assay for recombinant EphB3, using a different substrate, reported inhibition of PP2 with an IC50 value of 0.8 μM[14]. At 10 μM, 80% inhibition by PP2 was reproducibly observed and used for HTS as a positive control for every screening plate.

EphB3 Kinase Inhibitor Compounds

The EphB3 kinase inhibitor compounds include pyrazolo[1,5-a]pyridine derivatives and imidazo[1,2-a]pyridine derivatives. Examples of EphB3 kinase inhibitor compounds are described below.

Compounds of Formula (III) were tested for EphB3 tyrosine kinase inhibition by measuring the IC50 value for inhibiting EphB3 phosphorylation of the BTK peptide (SEQ ID NO:4) according to the assay described in Examples 1-6. Table 1 shows the structures of various pyrazolo[1,5-a]pyridine compounds and the corresponding IC50 values measured for each compound.

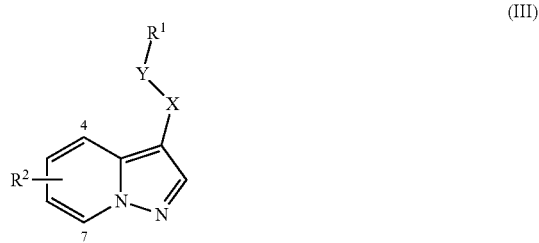

(III)

TABLE 1

Pyrazolo[1,5-a]pyridine compounds and IC50 values for inhibiting EphB3 phosphorylation of the BTK peptide (SEQ ID NO: 4)

| Cmpd | X | Y | R¹ | R² | IC$_{50}$ (μM) |
|---|---|---|---|---|---|
| 1 | C=O | NH | 2-Cl—Ph | H | 1.0 |
| 187598 | C=O | NH | Ph | H | NA |
| 187599 | C=O | NH | 2-F—Ph | H | ~20 |
| 187600 | C=O | NH | 3-Cl—Ph | H | NA |
| 187601 | C=O | NH | 4-Cl—Ph | H | NA |
| 187602 | C=O | NH | 2,3-Cl2—Ph | H | ~20 |
| 187605 | C=O | NH | 2-OMe—Ph | H | NA |
| 192653 | C=O | NH | 2-CF3—Ph | H | >20 |
| 192654 | C=O | NH | 2-CN—Ph | H | >20 |
| 192655 | C=O | NH | 2-MeSO2Ph | H | NA |
| 187597 | C=O | NMe | 2-Cl—Ph | H | NA |
| 187604 | C=O | NH | CH2-2-Cl—Ph | H | NA |
| 192659 (7) | NH | C=O | 2-Cl—Ph | H | >20 |
| 192661 | CH2 | NH | 2-Cl—Ph | H | >20 |
| 193691 | C=O | NH | 2-Cl—Ph | 4-Me | ~15 |
| 193692 | C=O | NH | 2-Cl—Ph | 5-Me | 0.26 |
| 193693 | C=O | NH | 2-Cl—Ph | 6-Me | ~15 |
| 193694 | C=O | NH | 2-Cl—Ph | 7-Me | NA |

TABLE 1-continued

Pyrazolo[1,5-a]pyridine compounds and IC50 values for inhibiting EphB3 phosphorylation of the BTK peptide (SEQ ID NO: 4)

| Cmpd | X | Y | R¹ | R² | IC$_{50}$ (μM) |
|---|---|---|---|---|---|
| 193698 | C=O | NH | 2-Cl—Ph | 4-Cl | ~20 |
| 193699 | C=O | NH | 2-Cl—Ph | 5-Cl | 2.0 |
| 193700 | C=O | NH | 2-Cl—Ph | 6-Cl | >20 |
| 193707 | C=O | NH | 2-Cl—Ph | 5-OMe | <0.2 |
| 193708 | C=O | NH | 2-Cl—Ph | 5-Ph | <0.1 |
| 193709 | C=O | NH | 2-Cl—Ph | 5-NMe2 | <0.1 |
| 193710 | C=O | NH | 2-Cl—Ph | 5-OBn | ~20 |
| 194727 | C=O | NH | 2-Cl—Ph | 5-Pyr | <0.3 |
| 194728 | C=O | NH | 2-Cl—Ph | 5-Morph | <0.3 |
| 194729 | C=O | NH | 2-Cl—Ph | 5-Pip | <0.1 |

NA: Not active at 20 μM;
Pyr = pyrrolidinyl;
Morph = morpholinyl;
Pip = piperidinyl A number of EphB3 tyrosine kinase inhibitor compounds of Formula (III) were identified. The ability of compounds of Formula (III) to inhibit EphB3 phosphorylation of the BTK peptide (SEQ ID NO:4) depends on the identity of X, Y, R₁ and R₂, as well as the type and position of substitution in R₁ and R₂.

With respect to R₁, compounds of Formula (III) having as R₁ a substituted aryl group can have EphB3 tyrosine kinase inhibitor activity. For example, compounds having R₁ as a phenyl group substituted at the 2-position with an electron withdrawing group (e.g., compounds 1, 187599, 187602, 192653, 192654) showed EphB3 tyrosine kinase inhibitor activity. In contrast, other compounds of Formula (III) having R₁ as an unsubstituted phenyl group (e.g., compound 187598), phenyl groups substituted with a halogen at the 3- or 4-positions (e.g., compounds 187600, 187601), a phenyl group having a methoxy (electron donor) group substitution at the 2-position (e.g., compound 187605), and a benzyl alkylaryl moiety having a halogen at the 2-aryl position (e.g., compound 187604) showed little or no inhibition of EphB3 phosphorylation of the BTK peptide (SEQ ID NO:4).

With respect to X and Y, compounds having a carbonyl moiety (CO) at X and a secondary amino moiety (—NH—) at Y showed EphB3 tyrosine kinase inhibitor activity. In addition, compounds having X as a secondary amino moiety and Y as a carbonyl moiety (e.g., compound 192659), as well as compounds with X as a lower alkyl (e.g., —CH2-) and Y as a secondary amino moiety also showed limited EphB3 tyrosine kinase inhibitor activity (e.g., compound 192661). For example, compound 1 (X is CO, Y is NH, R1 is 2-chlorophenyl, R2 is hydrogen) has an IC50 of 1.0 micromolar for inhibition of EphB3 phosphorylation of the BTK peptide (SEQ ID NO:4). Changing Y to a tertiary methylamino moiety (compound 187597) or substituting 2-chlorobenzyl for 2-chlorophenyl at R1 (compound 187604) rendered compound 1 inactive for inhibition of EphB3 phosphorylation of the BTK peptide (SEQ ID NO:4). Switching X and Y in compound 1 (i.e., X as NH and Y as CO) (compound 192659 (7)) or substituting a —CH2-alkyl group for X (compound 192661) both reduced the activity of compound 1 to an IC50 value of more than 20 micromolar for inhibition of EphB3 phosphorylation of the BTK peptide (SEQ ID NO:2).

To provide compounds of Formula (III) that inhibit EphB3 phosphorylation of the BTK peptide (SEQ ID NO:4), R₂ in Formula (III) can be a moiety providing steric hinderance positioned at the 5-position of the pyrazolo[1,5-a]pyridine heteroaromatic ring structure. For example, R₂ can be positioned at the 5-position and can be selected from the group consisting of hydrogen, halogen, lower ($C_1$-$C_8$) alkyl (e.g., methyl), alkoxy (e.g., methoxy), amino, aminoalkyl (e.g., dimethylamino), cycloalkyl, cycloheteroalkyl (e.g., pyrrolidinyl, piperidinyl, morpholinyl, and the like), aryl (e.g., phenyl), and oxyaryl (e.g., oxybenzyl). Other EphB3 kinase inhibitor compounds of Formula (III) can have $R_2$ positioned at the 4 or 6 positions (e.g., where $R_2$ is methyl or halogen).

Accordingly, the EphB3 kinase inhibitor compound can be a pyrazolo[1,5-a]pyridine derivative. In particular, the EphB3 kinase inhibitor compound can have the Formula (Ib):

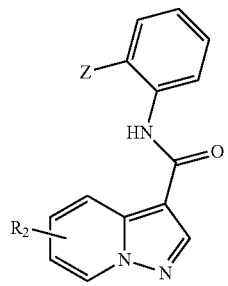

(Ib)

where Z is an electron withdrawing group and $R_2$ is selected from the group consisting of halogen, lower ($C_1$-$C_8$) alkyl, alkoxy, amino, aminoalkyl, cycloalkyl, cycloheteroalkyl, aryl, oxyaryl, and heteroaryl. The electron withdrawing group can be selected from the group consisting of: a halogen (e.g., chlorine, fluorine), a fluorocarbon (e.g., —$CF_3$), a cyano (—CN). In some embodiments, Z is an electron withdrawing group and $R_2$ is selected from the group consisting of lower ($C_1$-$C_8$) alkyl, alkoxy, amino, aminoalkyl, cycloalkyl, cycloheteroalkyl, aryl, oxyaryl, and heteroaryl.

Particularly preferred examples of these EphB3 kinase inhibitor compounds have the Formula (Ic):

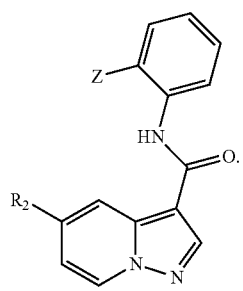

(Ic)

In some embodiments, Z can be a halogen moiety and $R_2$ can be selected from the group consisting of methyl, halogen, methoxy, amino, aminoalkyl, phenyl, benzyloxy, pyrrolidinyl, morpholinyl, and piperidinyl. For example, Z can be selected from the group consisting of chlorine and fluorine; and $R_2$ can be selected from the group consisting of hydrogen, methyl, halogen, methoxy, amino, aminoalkyl, phenyl, benzyloxy, pyrrolidinyl, morpholinyl, and piperidinyl. In particular, an EphB3 kinase inhibitor compound can be selected from the group consisting of:

a. N-(2-chlorophenyl)-5-methylpyrazolo[1,5-a]pyridine-3-carboxamide;
b. 5-chloro-N-(2-chlorophenyl)pyrazolo[1,5-a]pyridine-3-carboxamide;
c. N-(2-chlorophenyl)-5-methoxypyrazolo[1,5-a]pyridine-3-carboxamide;
d. 5-(benzyloxy)-N-(2-chlorophenyl)pyrazolo[1,5-a]pyridine-3-carboxamide;
e. N-(2-chlorophenyl)-5-(dimethylamino)pyrazolo[1,5-a]pyridine-3-carboxamide;
f. N-(2-chlorophenyl)-5-phenylpyrazolo[1,5-a]pyridine-3-carboxamide;
g. N-(2-chlorophenyl)-5-(pyrrolidin-1-yl)pyrazolo[1,5-a]pyridine-3-carboxamide;
h. N-(2-chlorophenyl)-5-morpholinopyrazolo[1,5-a]pyridine-3-carboxamide; and
i. N-(2-chlorophenyl)-5-(piperidin-1-yl)pyrazolo[1,5-a]pyridine-3-carboxamide.

Formula (IV) and Table 2 show the structures of an imidazo[1,2-a]pyridine EphB3 kinase inhibitor compound (193664) and various other heterocyclic compounds tested for EphB3 tyrosine kinase inhibition, along and $IC_{50}$ values for inhibiting EphB3 phosphorylation of the BTK peptide (SEQ ID NO:4) according to the assay described in Examples 1-6.

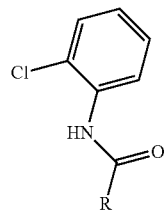

(IV)

TABLE 2

Various Candidate Compounds with IC50 values for inhibiting EphB3 phosphorylation of the BTK peptide (SEQ ID NO: 4)

| Cmpd | R | $IC_{50}$ (μM) |
| --- | --- | --- |
| 187608 | 3-indolyl[a] | NA |
| 187609 | N-methyl-3indolyl | NA |
| 187611 | 4-quinolinyl | NA |
| 193671 | 3-(1,2-benzisoxazolyl) | NA |
| 193672 | $R^1$ | >20 |
| 193673 | 3-(1H-indazolyl)[b] | >20 |
| 193695 | $R^{2, b}$ | NA |
| 193696 | $R^3$ | ~15 |
| 193697 | $R^4$ | NA |
| 193664 | $R^{5, b}$ | <0.5 |

[a]Prepared by EDCI mediated coupling of indole-3-carboxylic acid with 2-chloroaniline;
[b]Method C, steps d and e;
NA: Not active at 20 μM.

$R^1$ = 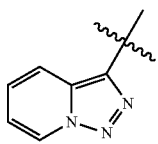

$R^2$ = 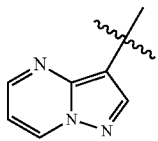

TABLE 2-continued

Various Candidate Compounds with IC50 values for inhibiting
EphB3 phosphorylation of the BTK peptide (SEQ ID NO: 4)

| Cmpd | R | IC$_{50}$ (μM) |
|---|---|---|

$R^3 =$ 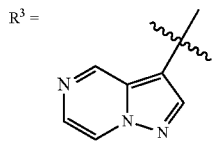 [SMILES: *c1cnn2ccncc12]

$R^4 =$ 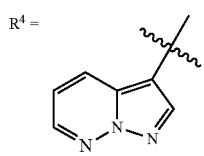 [SMILES: *c1cnn2ncccc12]

$R^5 =$ 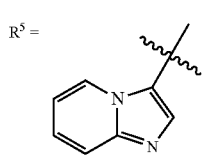 [SMILES: *c1cnc2ccccn12]

Accordingly, additional examples of EphB3 kinase inhibitor compounds include compounds of Formula (IV) where R is selected from the group consisting of: [1,2,3]triazolo[1,5-a]pyridinyl, pyrazolo[1,5-a]pyrazinyl, and imidazo[1,2-a]pyridinyl.

Formula (V) and Table 3 show the structures of various imidazo[1,2-a]pyridine EphB3 kinase inhibitor compounds and other compounds tested for EphB3 tyrosine kinase inhibition, along and IC50 values for inhibiting EphB3 phosphorylation of the BTK peptide (SEQ ID NO:4) according to the assay described in Examples 1-6.

(V)

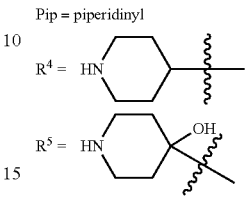

TABLE 3

Imidazo[1,2-a]pyridine compounds and IC50 values for inhibiting
EphB3 phosphorylation of the BTK peptide (SEQ ID NO: 4)

| Cmpd | R$^1$ | R$^2$ | R$^3$ | IC$_{50}$ (μM) |
|---|---|---|---|---|
| 209925 | Cl | H | Br | <0.2 |
| 209926 | Cl | H | Ph | <0.1 |
| 209927 | Cl | H | Pip | <0.1 |
|  | Cl | H | 4-ClPh |  |
| 209954 | OMe | H | Ph | >20 |
| 25 | Cl | Me | Ph | >20 |

TABLE 3-continued

Imidazo[1,2-a]pyridine compounds and IC50 values for inhibiting
EphB3 phosphorylation of the BTK peptide (SEQ ID NO: 4)

| Cmpd | R$^1$ | R$^2$ | R$^3$ | IC$_{50}$ (μM) |
|---|---|---|---|---|
| 211904 | Cl | H | R$^4$ | <0.1 |
|  | Cl | H | R$^5$ | <0.3 |

Pip = piperidinyl $R^4 =$ 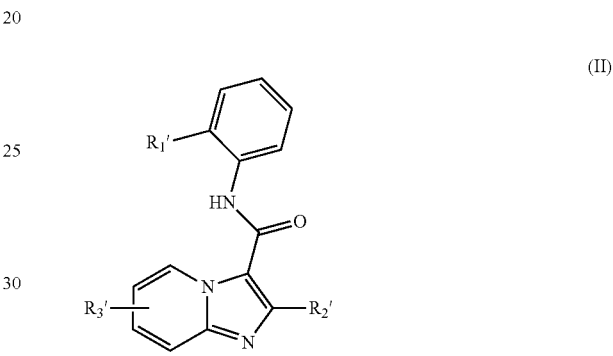

$R^5 =$

Some EphB3 kinase inhibitor compounds have the Formula (II):

(II)

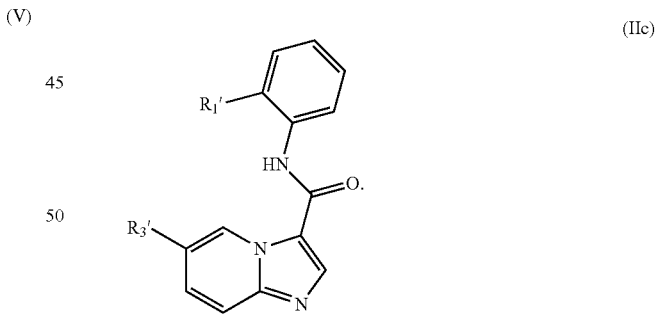

wherein R$_1$' is an electron withdrawing moiety, R$_2$' is selected from the group consisting of hydrogen and lower (C$_1$-C$_8$) alkyl; and R$_3$' is hydrogen, halogen, cycloalkyl, cycloheteroalkyl, aryl, and heteroaryl.

Particularly preferred examples of these EphB3 kinase inhibitor compounds have the Formula (IIc):

(IIc)

In some embodiments, R$_1$' can be a halogen moiety and R$_3$' can be selected from the group consisting of hydrogen, halogen, heterocycloalkyl, and aryl. For example, R$_3$' can be selected from the group consisting of hydrogen, halogen, phenyl, 4-chlorophenyl, 1-piperidinyl, 4-piperidinyl, and 4-piperidin-4-olyl. Preferably, R$_1$' is chlorine and R$_3$' is selected from the group consisting of hydrogen, bromine, phenyl, 1-piperidinyl, 4-piperidinyl, and 4-piperidin-4-olyl. In particular, the compound can be selected from the group consisting of:
a. 6-bromo-N-(2-chlorophenyl)imidazo[1,2-a]pyridine-3-carboxamide;

b. N-(2-chlorophenyl)-6-phenylimidazo[1,2-a]pyridine-3-carboxamide;
c. N-(2-chlorophenyl)-6-(4-chlorophenyl)imidazo[1,2-a]pyridine-3-carboxamide;
d. N-(2-methoxyphenyl)-6-phenylimidazo[1,2-a]pyridine-3-carboxamide;
e. N-(2-chlorophenyl)-2-methyl-6-phenylimidazo[1,2-a]pyridine-3-carboxamide;
f. N-(2-chlorophenyl)-6-(piperidin-4-yl)imidazo[1,2-a]pyridine-3-carboxamide; and
g. N-(2-chlorophenyl)-6-(4-hydroxypiperidin-4-yl)imidazo[1,2-a]pyridine-3-carboxamide.

Synthesis of EphB3 Kinase Inhibitor Compounds

The synthesis of many pyrazolo[1,5-a]pyrimidine derivatives was accomplished according to Scheme 1 (Method A). Pyrazolo[1,5-a]pyrimidine-3-carboxylic acid, 2, was converted to the corresponding acyl chloride and then treated with amines to give 3. Derivatives incorporating other heterocycles in place of the pyrazolo[1,5-a]pyrimidine were prepared in a similar manner, unless otherwise noted. The amide could be reduced with LiAlH$_4$ to give amine 4.

Scheme 1 (Method A):

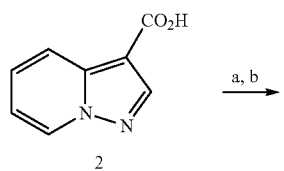

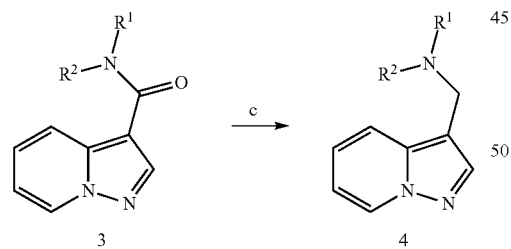

Reagents and conditions:
(a) (C=O)$_2$Cl$_2$, DCM, cat. DMF, 0° C. to rt, 2 h;
(b) R$^1$R$^2$NH, DCM, DIPEA, rt, 18 h;
(c) LiAlH$_4$, THF, Δ, 2 h.

Carboxylic acid 2 was also allowed to react with (PhO)$_2$P(O)N$^3$ to generated the corresponding acyl azide, which upon heating in the presence of benzyl alcohol underwent a Curtius rearrangement followed by alcohol addition to the intermediate isocyanate to produce 5 (Scheme 2, Method B).[8] Deprotection of the benzyl carbamate in the presence of hydrogen (1 atm) and 10% Pd/C yielded amine 6, which upon treatment of benzoyl chlorides gave 7.

Scheme 2 (Method B).

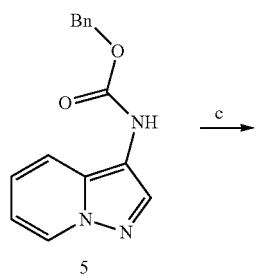

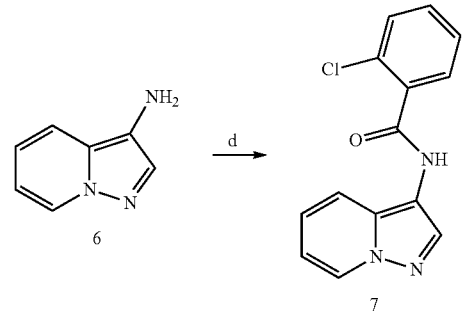

(a) (PhO)$_2$P(O)N$_3$, THF, DIPEA, rt, 16 h;
(b) BnOH, Δ, 12 h, 80% for two steps;
(c) H$_2$ (1 atm), 10% Pd/C, MeOH/EtOAc (1:1), 45 min;
(d) 2-Cl—PhC(O)Cl, DCM, DIPEA, rt, 16 h, 36% over two steps.

The synthesis of substituted pyrrolo[1,2-a]pyrimidines and derivatives that incorporate additional nitrogen atoms into the pyrrolo[1,2-a]pyrimidine is illustrated in Scheme 3 (Method C). Heterocycles 8 were converted to the N-amino derivatives 9 with MesitylSO$_3$NH$_2$.[9] Cycloaddition with methyl propiolate in the presence of potassium carbonate gave 10 in low yield.[10] Hydrolysis of the esters yielded 11. Conversion of the carboxylic acids to the corresponding acyl chlorides with thionyl chloride followed by treatment with 2-chloroaniline in pyridine gave 12.

Scheme 3 (Method C).

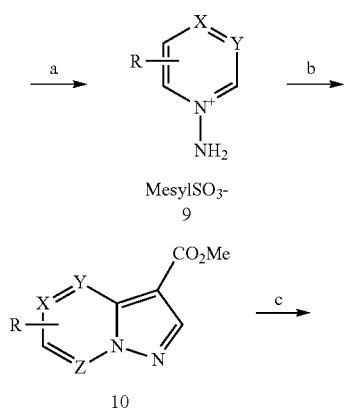

X = CH or N
Y = CH or N
Z = CH or N

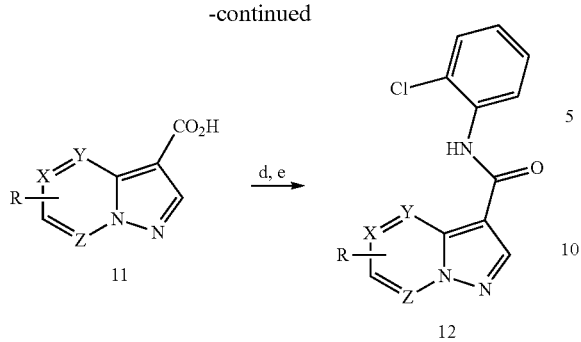

(a) MesitylSO₃NH₂, DCM, 0° C. to rt, 30 min, 81%;
(b) CH≡CCO₂Me, K₂CO₃, DMF, 50° C., 72 h, 14%;
(c) LiOH, MeOH/H₂O, rt, 2 h, then 1N HCl, 85-90%;
(d) SOCl₂, 80° C., 1 h;
(e) 2-ClPhNH₂, pyridine, rt, 16 h.

The synthesis of 5-amino substituted pyrazolo[1,5-a]pyridine derivatives is outlined in Scheme 4 (Method D). 4-Chloropyridinium hydrochloride, 13, was treated with an amine to generate 14, via a nucleophilic aromatic substitution. Conversion of 14 to the N-aminopyridine 15 with 2,4-(NO₂)₂PhONH₂ followed by cycloaddition with N-(2-chlorophenyl)-2-propynamide 11 produced 16.

The synthesis of imidazo[1,2-a]pyridine derivatives was accomplished according to Scheme 5 (Method E). 2-Amino-5-bromopyridine, 17, was coupled with phenyl boronic acid to give 18. 5-Bromo-2-nitropyridine, 19, was treated with piperidine to give 20, which was subsequently hydrogenated in the presence of 10% Pd/C to give 21. The 2-aminopyridines 18 or 21 were heated at reflux in toluene with N,N-dimethylformamide dimethyl acetal (DMF-DMA) and then treated with 2-bromo-N-arylacetamides (prepared by coupling anilines with 2-bromoacetyl chloride) to give 22 (See, e.g., Kullander K, Klein R: Mechanisms and Functions of Eph and Ephrin Signaling. *Nature Rev. Mol. Cell Biol* 2002; 3:475-486). β-Ketoamide 23 was chlorinated with sulfuryl chloride to give 24, which was used without purification. Heating 24 in the presence of 17 and sodium bicarbonate gave the 2-methyl imidazo[1,2-a]pyridine derivative 25.

The synthesis of several other 5-substituted imidazo[1,2-c]pyridine derivatives was accomplished according to the method outlined in Scheme 6 (Method F). A Pd-mediated coupling of boronic ester 26 with 2-amino-5-bromopyridine, 27, followed by hydrogenation yielded 28. Amine 27 was also converted to intermediate 29, which was not isolated, but subjected to halogen metal exchange with n-BuLi followed by addition of N-Boc-4-piperidone to give 30. Both 28 and 30 were converted to 31 and 32, respectively, utilizing the sample procedure described in Method E. Finally, removal of the carbamate protecting groups from 31 and 32 with 30% TFA in dichloromethane gave amines 33 and 34, respectively.

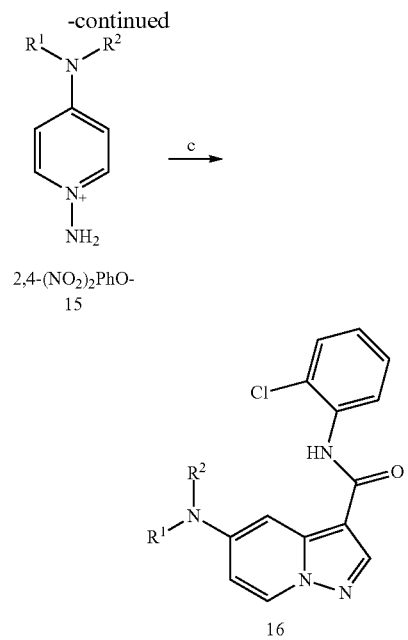

(a) HNR¹R², H₂O, MW, 130° C., 30 min, 90%;
(b) 2,4-(NO₂)₂PhONH₂, CH₃CN, Δ, 16 h, 81%;
(c) CH≡CC(O)NH-2-ClPh, K₂CO₃, DMF, 50° C., 72 h.

Scheme 5 (Method E).

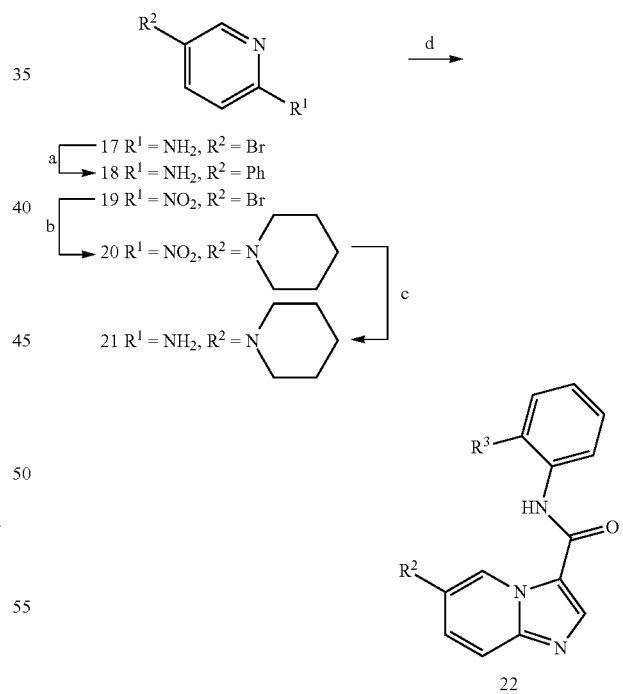

Scheme 4 (Method D).

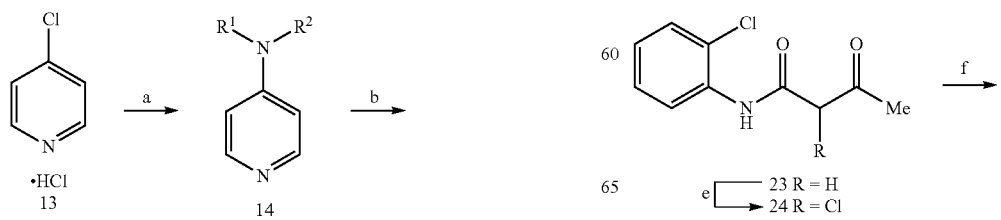

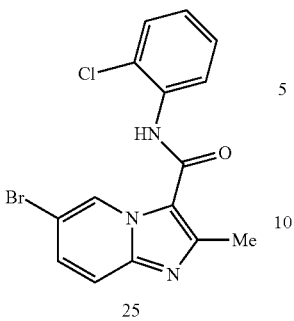

25

(a) PhB(OH)$_2$, Pd(PPh$_3$)$_4$, Na$_2$CO$_3$, CH$_3$CN, H$_2$O;
(b) Piperidine, DMSO, n-Bu$_4$NI, K$_2$CO$_3$, 95° C.
(c) H$_2$ (1 atm), 10% Pd/C, EtOH/MeOH, rt
(d) Me$_2$NCH(OMe)$_2$, toluene, Δ, 6 h then BrCH$_2$C(O)NH-2-R—Ph (where R = Cl or OMe), MeOH, Δ;
e) SO$_2$Cl$_2$, 0° C. to rt;
f) 17, toluene, NaHCO$_3$, 120° C.

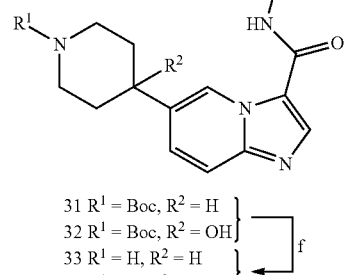

31 R$^1$ = Boc, R$^2$ = H
32 R$^1$ = Boc, R$^2$ = OH  } f
33 R$^1$ = H, R$^2$ = H
34 R$^1$ = H, R$^2$ = OH (a) 27, Pd(PPh$_3$)$_4$, Na$_2$CO$_3$, CH$_3$CN, H$_2$O, 90° C.;
(b) 10% Pd/C, H$_2$ (1 atm), EtOH;
(c) n-BuLi (2 equiv), (Me$_2$SiClCH$_2$)$_2$, THF, -78° C., 1 h;
(d) n-BuLi (1 equiv), N-Boc-4-piperidone, -78° C. to rt, 18 h,;
e) DMF-DMA, 85° C., toluene 8 h, then BrCH$_2$C(O)NH-2-R—Ph, MeOH, 85° C., 18 h;
f) 30% TFA in DCM, 1 h, rt.

EphB3 Kinase Inhibiting Pharmaceutical Compositions and Administration

Pharmaceutical compositions can comprise a therapeutically effective dose of one or more EphB3 Kinase Inhibitor compounds. The pharmaceutical compositions also may comprise suitable solid or gel phase carriers or excipients. A pharmaceutical preparation can include a mixture of one or more EphB3 Kinase Inhibitor compounds mixed with and/or coated with a carrier substance. The EphB3 Kinase Inhibitor compounds can be administered on their own or as a pharmaceutical composition comprising the EphB3 Kinase Inhibitor compound in combination with a pharmaceutically acceptable diluent, adjuvant and/or carrier.

The EphB3 Kinase Inhibitor compound may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

The dose of the EphB3 Kinase Inhibitor compound to be administered will depend on the relevant indication, the age, weight and gender of the patient, and the route of administration of the compound, and can be determined by a physician. For example, the dosage can preferably be in the range of from 0.01 mg/kg to 10 mg/kg.

The EphB3 Kinase Inhibitor compounds can be administered systemically (e.g. by oral administration in the form of tablets, pills, capsules, syrups, powders, granules, and the like). For oral administration as a tablet, paste or liquid, the active compound can be admixed with an adjuvant or a carrier, e.g. lactose, saccharose, sorbitol, mannitol; a starch, e.g. potato starch, corn starch or amylopectin; a cellulose derivative; a binder, e.g. gelatin or polyvinylpyrrolidone, and/or a lubricant, e.g. magnesium stearate, calcium stearate, polyeth- Scheme 6 (Method F).

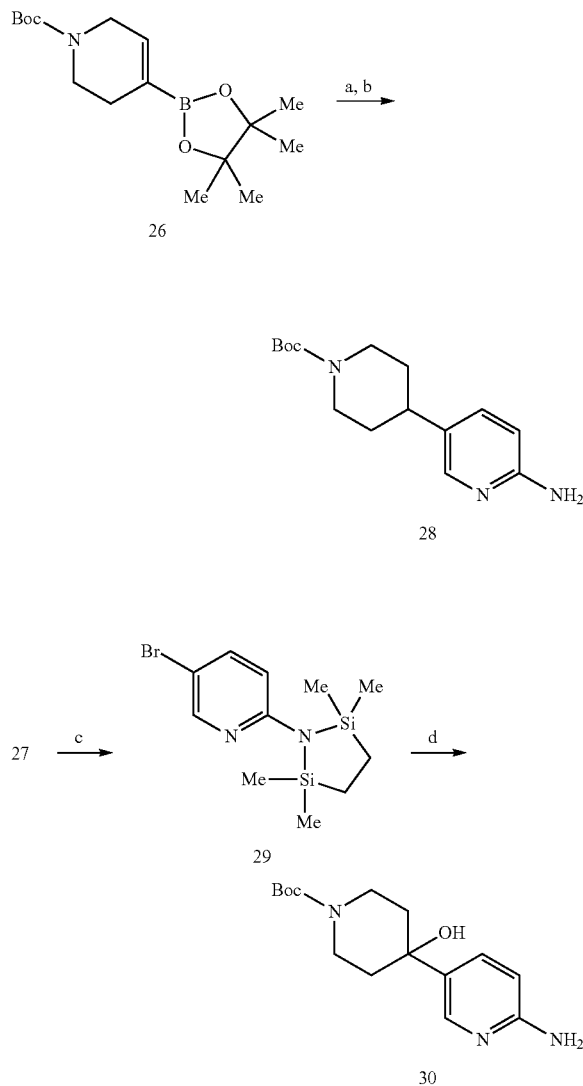

ylene glycol, a wax, paraffin, and the like, and then compressed into tablets. If coated tablets are required, the cores, prepared as described above, can be coated with a concentrated sugar solution which can contain e.g. gum arabic, gelatin, talcum, titanium dioxide, and the like. Alternatively, the tablet can be coated with a suitable polymer dissolved in a readily volatile organic solvent. For the preparation of soft gelatin capsules, the compound can be admixed with e.g. a vegetable oil or polyethylene glycol. Hard gelatin capsules can contain granules of the compound using either the above mentioned excipients for tablets. Also liquid or semisolid formulations of the drug can be filled into hard gelatin capsules.

Liquid preparations for oral application can be in the form of syrups or suspensions, for example solutions containing the compound, the balance being sugar and a mixture of ethanol, water, glycerol and propylene glycol. Optionally such liquid preparations can contain coloring agents, flavoring agents, saccharine and/or carboxymethylcellulose as a thickening agent or other excipients known to those skilled in art.

The EphB3 Kinase Inhibitor compounds can be administered to the lung and/or the airways (e.g., in the form of solutions, suspensions, HFA aerosols or dry powder formulations). In one example, pharmaceutical formulations comprising the EphB3 Kinase Inhibitor compounds can be administered using an inhaler device. Dry powder formulations and pressurized HFA aerosols of the compounds can be administered by oral or nasal inhalation. For inhalation the EphB3 Kinase Inhibitor compound can be finely divided. The finely divided compound preferably has a mass median diameter of less than 10 µm, and can be suspended in a propellant mixture with the assistance of a dispersant, such as a C8-C20 fatty acid or salt thereof, (e.g. oleic acid), a bile salt, a phospholipid, an alkyl saccharide, a perfluorinated or polyethoxylated surfactant, or other pharmaceutically acceptable dispersant. The finely divided powder can be formed into spheres which break up during the inhalation procedure. This spheronized powder can be filled into the drug reservoir of a multidose inhaler. With this system the active compound, with or without a carrier substance, is delivered to the patient. The inhaler can be a single or a multi dose inhaler, and can be a breath actuated dry powder inhaler.

A pharmaceutical composition can include an EphB3 Kinase Inhibitor compound and be formulated for parenteral administration (e.g. in the form of sterile parenteral solutions or suspensions). Preparations for parenteral administration of a compound of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The pharmaceutical compositions can include the EphB3 Kinase Inhibitor compound and a buffering agent. Suitable buffering agents include: acetic acid and a salt (1-2 percent w/v); citric acid and a salt (1-3 percent w/v); boric acid and a salt (0.5-2.5 percent w/v); and phosphoric acid and a salt (0.8-2 percent w/v). Suitable preservatives include benzalkonium chloride (0.003-0.03 percent w/v); chlorobutanol (0.3-0.9 percent w/v); parabens (0.01-0.25 percent w/v) and thimerosal (0.004-0.02 percent w/v).

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate injection suspensions. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Other pharmaceutical compositions including EphB3 Kinase Inhibitor compounds can be formulated for rectal administration (e.g. in the form of suppositories containing conventional suppository bases such as cocoa butter or other glycerides.).

Pharmaceutical compositions comprising an EphB3 Kinase Inhibitor compound can be administered by a variety of administration routes, including by delivery methods that deliver the EphB3 Kinase Inhibitor compound to a desired site within a subject. Unless otherwise indicated, "administering" a pharmaceutical composition can be accomplished by any means known to the skilled artisan. Preferred routes of administration include but are not limited to oral, parenteral, intralesional, topical, transdermal, intramuscular, intranasal, intratracheal, inhalational, ocular, vaginal, and rectal. The particular mode selected will depend, of course, upon the particular adjuvants or antigen selected (depending upon the method employed), the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

A method of treating cancer or a neuronal system injury is further provided, the method comprising administering to a subject a therapeutically effective amount of an EphB3 kinase inhibitor compound to mitigate or prevent the medical condition, the EphB3 kinase inhibitor compound being selected from the group consisting of compounds of formula (I) and formula (II):

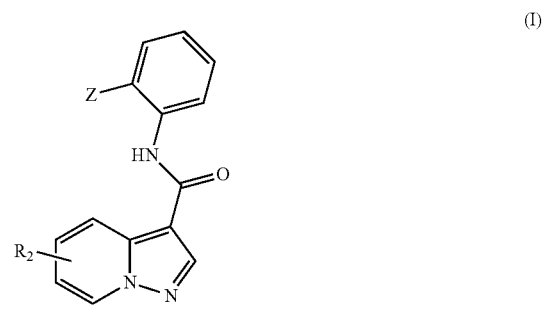

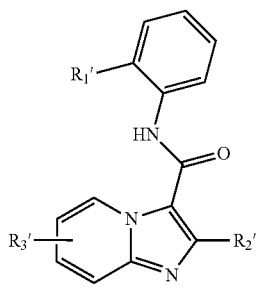

(II)

or a pharmaceutically acceptable salt thereof, wherein:

$R_1'$ and Z are each independently an electron withdrawing group;

$R_2$ is selected from the group consisting of hydrogen, halogen, lower ($C_1$-$C_8$) alkyl, amino, alkoxy, aminoalkyl, cycloalkyl, cycloheteroalkyl, aryl, oxyaryl, and heteroaryl;

$R_2'$ is selected from the group consisting of hydrogen and lower ($C_1$-$C_8$) alkyl; and $R_3'$ is selected from the group consisting of hydrogen, halogen, cycloalkyl, cycloheteroalkyl, aryl, and heteroaryl.

In some embodiments, the method is a method of treating cancer. In some embodiments, the cancer is selected from the group consisting of leukemia, non-small cell lung cancer, colon cancer, CNS cancer, melanoma, ovarian cancer, renal cancer, prostate cancer, and breast cancer.

In some embodiments, the method is a method of treating a neuronal system injury. In some embodiments, the neuronal system injury is a central nervous system injury selected from the group consisting of cerebral ischemia and traumatic brain injury.

The methods can use any of the EphB3 kinase inhibitor compounds described herein. Accordingly, in some embodiments, the EphB3 kinase inhibitor compound is selected from the group consisting of compounds of formula:

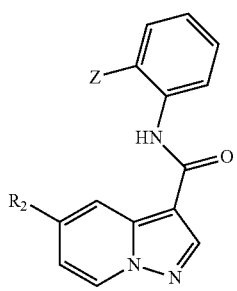

and pharmaceutically acceptable salts thereof.

In some embodiments:

Z is chlorine; and $R_2$ is selected from the group consisting of hydrogen, methyl, halogen, methoxy, amino, aminoalkyl, phenyl, oxybenzyl, pyrrolidinyl, morpholinyl, and piperidinyl.

In some embodiments, $R_2$ is selected from the group consisting of chlorine, methyl, methoxy, phenyl, dimethylamino, pyrrolidinyl, morpholinyl and piperidinyl.

In some embodiments, the EphB3 kinase inhibitor compound is selected from the group consisting of compounds of formula:

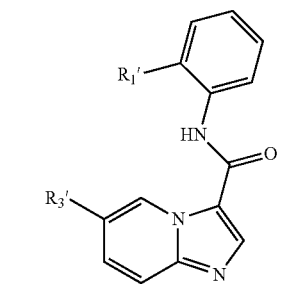

and pharmaceutically acceptable salts thereof.

In some embodiments:

$R_1'$ is chlorine; and $R_3'$ is selected from the group consisting of hydrogen, halogen, heterocycloalkyl, and aryl.

In some embodiments, $R_3'$ is selected from the group consisting of hydrogen, chlorine, phenyl, 4-chlorophenyl, 1-piperidinyl, 4-piperidinyl, and 4-piperidin-4-olyl.

A method of treating neuronal system injury is further provided, the method comprising administering to a subject a therapeutically effective amount of an EphB3 kinase inhibitor compound to mitigate or prevent the medical condition, wherein the EphB3 kinase inhibitor compound has an $IC_{50}$ for inhibiting EphB3 phosphorylation of the BTK peptide (SEQ ID NO:4) of up to 1.0 micromolar.

In some embodiments, the neuronal system injury is a central nervous system injury selected from the group consisting of cerebral ischemia and traumatic brain injury; and the EphB3 kinase inhibitor compound has an $IC_{50}$ for inhibiting EphB3 phosphorylation of the BTK peptide (SEQ ID NO:4) by an EphB3 kinase of up to about 0.5 micromolar, the EphB3 kinase being selected from the group consisting of: SEQ ID NO:1, SEQ ID NO:2 and SEQ ID NO:3.

Methods of treating a medical condition associated with erythropoietin-producing hepatocellular carcinoma receptor B3 can include administering to a subject a therapeutically effective amount of an EphB3 kinase inhibitor compound to mitigate or prevent the medical condition. The EphB3 kinase inhibitor compound preferably has an IC50 for inhibiting EphB3 phosphorylation of the BTK peptide (SEQ ID NO:4) of up to 1.0 micromolar. For instance, the medical condition can be cerebral ischemia, traumatic brain injury and other neurodegenerative conditions. The EphB3 kinase inhibitor compound can have an IC50 for inhibiting EphB3 phosphorylation of the BTK peptide (SEQ ID NO:4) of up to about 0.5 micromolar.

The present invention further provides a compound described herein (or any embodiment thereof), or a pharmaceutically acceptable salt thereof, for use in treatment of any of the disorders or disease states described herein. The present invention further provides use of a compound described herein (or any embodiment thereof), or a pharmaceutically acceptable salt thereof, for use in the preparation of a medicament for the treatment of any of the disorders or disease states described herein.

Unless otherwise defined, all technical and scientific terms used herein have the same meaning as commonly understood by one of ordinary skills in the art to which this invention belongs. Although methods and materials similar or equivalent to those described herein can be used in the practice or testing of the present invention, suitable methods and materials are described below.

ALL PUBLICATIONS, PATENT APPLICATIONS, PATENTS, AND OTHER REFERENCES MENTIONED HEREIN ARE INCORPORATED BY REFERENCE IN THEIR ENTIRETY

1. Pasquale, E. B. *Nat. Rev. Mol. Cell Biol.* 2005, 6, 462.
2. Kullander, K.; Klein, R. *Nat. Rev. Mol. Cell Biol.* 2002, 3, 475.
(a) Pasquale, E. B. *Cell,* 2008, 133, 38. (b) Himanen, J. P.; Saha, N.; Nikolov, D. B. *Curr. Opin. Cell. Biol.* 2007, 19, 534. (c) Aoto, J.; Chen, L. *Brain Res.* 2007, 1184, 72.
3. Holder, N.; Cooke, J.; Brennan, C. *Eur. J. Neurosci.* 1998, 10, 405.
4. Willson, C. A.; Foster, R. D.; Onifer, S. M.; Whittemore, S. R.; Miranda, J. D. *J. Mol. Hist.* 2006, 37, 369.
5. Liu, X.; Hawkes E.; Ishimaru, T.; Tran T.; Sretavan D. W. *J. Neurosci.* 2006, 26, 3087.
6. Willson, C. A.; Miranda, J. D.; Foster, R. D.; Onifer, S. M.; Whittemore, S. R. *Cell. Transplant.* 2003, 12, 279. (b) Miranda, J. D.; White, L. A.; Marcillo, A. E.; Willson, C. A.; Jagid, J.; Whittemore, S. R. *Exp. Neurol.* 1999, 156, 218.
7. Ninomiya, K.; Shioiri, T., Yamada S. *Tetrahedron* 1974, 30, 2009.
8. Tamura, Y; Minamikawa, J.; Miki, Y.; Matsugashita, S.; Ikeda, M. *Tetrahedron Lett.* 1972, 40, 4133.
9. Tamura, Y.; Sumida, Y.; Miki, Y.; Ikeda, M. *J. Chem. Soc., Perkin Trans.* 1 1975, 406.
10. Coppola, G. M.; Damon, R. E. *Syn. Comm.* 1993, 23, 2003.
11. Georgescu, F.; Georgescu, E.; Draghici, C.; Iuhas, P. C.; Filip, P. I. *Rev. Roumaine Chim.* 2005, 50, 349.
12. Kullander K, Klein R: Mechanisms and Functions of Eph and Ephrin Signaling. *Nature Rev. Mol. Cell Biol* 2002; 3:475-486.
13. Pasquale E B: Eph receptor signaling casts a wide net on cell behaviour. Nature 2005; 6:462-475.
14. Marler J R, Goldstein L B: Medicine. Stroke—tPA and the clinic. Science 2003; 301:1677.
15. Lo D C, McAllister A K, Katz L C: Neuronal Transfection in Brain Slices Using Particle—Mediated Gene Transfer. Neuron 1994; 13:1263-1268.
16. Lo D C: Neuronal transfection using particle-mediated gene transfer. Curr Protoc Neurosci 2001; Chapter 3:Unit 3.15.
17. Schurr A, Rigor B M: Emerging Strategies in Neuroprotection. Birkhauser, Boston, 1992: 24-43.
18. Wang J K, Portbury S, Thomas M B, Barney S, Ricca D J, Morris D L, Warner D S, Lo D C: Cardiac Glycosides Provide Neuroprotection Against Ischemic Stroke: Discovery by a Brain Slice-Based Compound Screening Platform. Proc Natl Acad Sci USA 2006; 103:10461-10466.
19. Albers G W, Atkinson R P, Kelley R E, Rosenbaum D M: Safety, Tolerability, and Pharmacokinetics of the N-Methyl-D-Aspartate Antagonist Dextorphan in Patients with Acute Stroke. Stroke 1995; 26:254-258.
20. Strausberg R L, Feingold E A, Klausner R D, Collins F S: The Mammalian Gene Collection. Science 1999; 286:455-457.
21. Yang J, Liu X, Bhalla K, Kim C N, Ibrado A M, Cai J, Peng T I, Jones D P, Wang X: Prevention of apoptosis by Bcl-2: release of cytochrome c from mitochondria blocked. Science 1997; 275:1129-32.
22. Takasu M A, Dalva M B, Zigmond R E, Greenberg M E: Modulation of NMDA Receptor-Dependent Calcium Influx and Gene Expression Through EphB Receptors. Science 2002; 295:491-495.
23. Lipinski C A, Lombardo F, Dominy B W, Feeney P J: Experimental and computational approaches to estimate solubility and permeability in drug discovery and development settings. Adv Drug Del Rev 1997; 23:3-25.
24. Zhang J H, Chung T D, Oldenburg K R: A simple statistical parameter for use in evaluation and validation of high throughput screening assays. J Biomol Screen 1999; 4:67-73.
25. Bembenek M E, Schmidt S, Li P, Morawiak J, Prack A, Jain S, Roy R, Parsons T, Chee L: Characterization of the Kinase Domain of Ephrin-B3 Receptor Kinase Using a Scintillation Proximity Assay. Assay Drug Development Technol 2003; 1: 555-563.

EXAMPLES

The invention is further described in the following examples, which do not limit the scope of the invention described in the claims.

Example 1

Assay to Identify EphB3 Kinase Inhibitor Compounds by Inhibition of EphB3 Phosphorylation of a BTK Peptide Recombinant human EphB3 kinase was purchased from Cell Signaling Technology (Danvers, Mass.). The enzyme was produced using a baculovirus expression system with a construct expressing human EphB3 (Gln585-Val998; GenBank accession No. NM_004443) and was amino-terminally fused to a GST-6-Thrombin cleavage site and purified by 1-step affinity purification using glutathione-agarose. The biotinylated tyrosine peptide substrate, BTK is a synthetic 17 amino acid sequence biotin-AGAGLKKVVALY*DYMPM, Y* was the site of phosphorylation (American Peptide, Sunnyvale, Calif.), reconstituted to a protein concentration of 500 uM in assay buffer and stored at −20 C. Detection reagents streptavidin-allophycocyanin (SA-XL665) and europium cryptate labeled anti-phosphotyrosine antibody 66 (PT66) were purchased from Cisbio, Inc. (Bedford, Mass.). Buffer constituents 4-(2-hydroxymethyl)-1-piperazeneethanesulfonic acid (Hepes), manganese chloride (MnCl2), dithiothreitol (DTT), glycerol, Tween 20, ethylenediamine tetraacetic acid (EDTA), potassium fluoride (KF), bovine serum albumin (BSA), and dimethyl sulfoxide (DMSO) were purchased from Sigma-Aldrich (St. Louis, Mo.). Kinase inhibitors staurosporine and PP2 were purchased from EMD Biosciences (San Diego, Calif.). Optimizations of the reaction conditions and compound testing were carried out in black 384-well low volume non-binding polystyrene plates from Corning Life Science (Lowell, Mass.). FRET signals were measured on a PerkinElmer Envision (Waltham, Mass.) calibrated with an HTRF Reader Control Kit purchased from Cisbio, Inc. [γ-33P]-ATP was from PerkinElmer (Boston, Mass.). Truncated recombinant human EphB3 kinase, (amino acids 623-907), was purchased from Invitrogen Corporation (Carlbad, Calif.) and stored at −80 C. Brain slice cultures were prepared as described in Wang et al 2006. In brief, enocortical brain slices were prepared from postnatal day 7 Sprague-Dawley rat pups, which were killed in accordance with National Institutes of Health guidelines. The cerebral cortex was dissected, cut into 400-um-thick slices and transferred into a container containing cold artificial cerebrospinal fluid with 1 µM MK-801. To mimic ischemic injury using transient oxygen-glucose deprivation (OGD) (Schurr, A. & Rigor, B. M. (1992) in Emerging Strategies in Neuroprotection, eds. Marangos, P. J. & Lal, H. (Birkhauser, Boston), pp. 24-43) slices from one hemisphere of each brain were exposed to glucose-free, $N_2$-bubbled artificial cerebrospinal fluid for 7.5 min in a low $O_2$ (<0.5%) environment. The OGD slices were then plated side-by-side with control slices from the contralateral hemisphere on nitrocellulose or Millicell (Millipore) permeable membranes, which were prepared identically except for no OGD. Thirty minutes after plating, the brain slice pairs were transfected (see *Biolistic Transfection*), transferred to 24-well plates, and incubated at 37° C. under 5% $CO_2$ in humidified chambers.

To assay the amount of neuronal cell degeneration and death after OGD, brain slice explants were transfected with yellow fluorescent protein (YFP) expression plasmids driven by the cytomegalovirus promoter (Gwiz,Genlantis), via biolistic particle-mediated gene transfer, to create a subpopulation of "sentinel" neurons as previously described (Lo in Current Protocols in Neuroscience, ref 46 in Wang paper). Gold particles (1.6 _m) were used as the DNA carrier (Strem Chemicals) with a DNA load of 2 ug of DNA per milligram of Au. After transfection, brain slices were transferred to 24-well plates containing culture medium.

Individual cDNAs were plasmid-prepped and coated onto gold-particles along with a YFP expression construct as an independent marker for cell viability.

Neuronal survival was scored as described previously in Wang et al (Wang et al., "Cardiac Glycosides Provide Neuroprotection Against Ischemic Stroke: Discovery by a Brain Slice-Based Compound Screening Platform," Proc Natl Acad Sci USA 2006; 103:10461-10466) by visual inspection after 24 and 48 h by using a Leica MZIIIFL fluorescence stereomicroscope equipped with appropriate filter sets. Surviving pyramidal neurons in the cortical brain slice explants were identified based on their characteristic position, orientation, and morphology. All labeled pyramidal neurons were counted in each cortical brain slice explant; therefore, values reported represent the total number of surviving pyramidal neurons per brain slice. Advantages of this screening approach included the ability to assay several sequential time points on the same sets of slices by using the vital marker yellow fluorescent protein (YFP) and the ability to identify specific neuronal cell types such as cortical pyramidal neurons based on dendritic morphology as described here. Moreover, visual scoring of numbers of healthy neurons constituted a quantitative assay with good dynamic range (from zero to hundreds of sentinel neurons per cortical brain slice explant) that was linear throughout this range and had essentially no background noise.

EphB3 Kinase Inhibitor Compounds were identified by screening candidate compounds using a Beckman Coulter Biomek FX (Beckman Coulter, Fullerton, Calif.) liquid handling station containing a 384-multichannel pipette head. Compound source plates for the assay were created prior to the screen. 0.4 µl of 5 mM test compound were added to columns 1-22 of a 384-well PCR plate (Axygen Scientific, Inc., Union City, Calif.). The plates were sealed with aluminum plate seals and stored at −20° C. Compound source plates were thawed to RT on the day of a screen and 40 µl of Hepes, pH 7.5 buffer was added to columns 1-22 with a Multidrop384 (ThermoFisher Scientific, Waltham, Mass.) to create a 50 µM compound intermediate at 1% DMSO. 40 µl of 1% DMSO prepared in Hepes buffer, pH 7.5 was added to columns 23 and 24, rows A-L for positive and negative enzyme controls. 40 µl of 30 µM PP2 was prepared in Hepes buffer, pH 7.5 as a positive compound control and added to columns 23-24, rows M-P. EphB3 and BTK were prepared fresh in 15 mM Hepes, pH 7.5 reaction buffer containing 1% glycerol, 0.01% Tween 20, 1.875 mM DTT, and 1.875 mM $MnCl_2$. The substrate was aliquoted into the wells of a 384-well nonbinding polystyrene plate (Corning Life Sciences, Lowell, Mass.) and kept at RT. EphB3 was prepared with ATP in ice cold buffer immediately before the start of an assay. The enzyme was aliquoted into columns 1-22 of a 384-well low volume nonbinding polystyrene plate and added to columns 23-24 for the positive enzyme (rows E-L) and compound (rows M-P) controls. Reaction buffer was aliquoted into columns 23-24, rows A-D for the negative control. To start an assay, 2 µl of 37.5 nM EphB3 kinase and 7.5 µM ATP was transferred to a 384-well reaction plate and 1 µl of compound intermediate or DMSO was added. The enzyme/ATP/compound was incubated at RT for 30 min. 3 µl of 1.2 µM BTK was added to initiate the enzymatic reaction where the final reaction concentrations were 12.5 nM EphB3, 600 nM BTK, 2.5 µM ATP, and 1.875 mM $MnCl_2$ with 16.7 µM test compound. After 1 hr, the reaction was stopped and phosphorylation detected with 18 µl of a quenching detection solution containing 33.3 mM EDTA, 150 nM SA-XL665, and 3 nM PT66 antibody in KF buffer. Assay plates were sealed with an aluminum plate seal and stored overnight at 4° C. HTRF signals were measured at 24 hr on an Envision plate reader. To eliminate interference with fluorescence readouts by variations in the optical density created by media constituents, the 665 nm emission signal was normalized to the europium cryptate 620 nm emission signal (665/620 Ratio) as described in equation 1. To compare samples between plates or separate experiments, a specific signal (Delta F) was calculated to minimize variability (equation 2). The Delta F (dF) was calculated as the ratio of the difference between the sample and negative control 665/620 ratios to the difference between the negative control ratio. The percent inhibition of a given test compound to the enzyme control was determined using Delta F values (equation 3).

$$665/620 \text{ Ratio (Ratio)} = (\text{Sample } Em_{665}/\text{Sample } Em_{620}) \times 10000 \quad \quad 1)$$

$$\text{Delta } F \ (dF) = 100 \times [(\text{Ratio}_{Sample} - \text{Ratio}_{Negative})/\text{Ratio}_{Negative}] \quad \quad 2)$$

$$\% \text{ Inhibition} = 100 \times \{1 - [(dF_{Sample} - dF_{Negative})/(dF_{Enzyme} - dF_{Negative})]\} \quad \quad 3)$$

Data from tested compounds was uploaded into an Oracle database using ActivityBase (IDBS, Bedford, Mass.) and stored. The '% inhibition' of a compound was calculated using the positive and negative enzyme controls within each plate. The z' factor was calculated to determine the quality of each plate and the quality of the screening run[13]. Compounds exhibiting greater than 60% inhibition were selected using SARgen query tool. The selected inhibitors were retested under compound testing conditions at 3-concentrations of 0.1, 1, and 10 µM in triplicate to confirm activity.

The IC50 value of each candidate compound for inhibiting Eph-B3 catalyzed BTK phosphorylation was measured by a [33]P Radiometric Assay. At 25° C. in a pH 7.5 buffer (50 mM Hepes, 2 mM DTT, 2 mM MnCl2, 0.01% Tween 20, 1% glycerol) various concentrations of test compounds (20 µM-10 nM) dissolved in DMSO were added to 7.5 nM EphB3 in reaction buffer and preincubated at 25 C for 30 min. EphB3 catalyzed BTK phosphorylation was initiated by the addition of a BTK/ATP stock solution to give final substrate concentrations of 500 nM BTK and 650 nM ATP. The ATP to [γ-33P]-ATP was kept constant at 1 µM ATP/0.8 µCi [γ-33P]-ATP. The reactions were conducted in duplicate in 96-well Streptavidin coated FlashPlates (PerkinElmer). After an incubation of 30 min at 25° C., the reaction was terminated by the addition of 25 mM EDTA and the streptavidin-bound BTK was washed 5 times with 75 mM phosphoric acid. The FlashPlate was then counted on a PerkinElmer 1450 MicroBeta Trilux scintillation counter. A background reaction was conducted in the absence of BTK peptide. Progress curves for production of phospho-BTK were linear for at least 30 min, allowing the calculation of initial velocities. IC50 values were calculated using Grafit software using a four parameter fit. A two parameter fit used is defined below:

$$v_{obs} = \frac{v_{control}}{1 + \left(\frac{[I]}{IC_{50}}\right)^n}$$

Example 2

Determination of Working Enzyme Concentration and Velocity

Enzyme velocity was determined at saturating substrate (6 µM) and ATP (25 µM) concentrations. Serial dilutions of EphB3 kinase, starting at 37.5 nM, was prepared in 15 mM Hepes, pH 7.5 reaction buffer containing 1% glycerol, 0.01% Tween 20, 1.875 mM DTT, 1.85 mM MnCl₂, and 75 µM ATP. 12 µM BTK was diluted separately in 15 mM Hepes, pH 7.5 buffer containing 1% glycerol, 0.01% Tween 20, 1.875 mM DTT, and 1.875 mM MnCl₂. 2 µl of enzyme/ATP was combined and incubated with 1 µl of 1% DMSO in Hepes buffer, pH 7.5 in a 384-well reaction plate for 30 min at room temperature (RT) to mimic compound treatment conditions for compound testing. The enzyme reaction was initiated with 3 µl of BTK where the final reaction concentrations were 6 µM BTK, 25 µM ATP, 1.875 mM MnCl2, and 0.33% DMSO with 12.5 nM or less EphB3. Reactions were run for 0, 5, 10, 15, 20, 30, 40, 60 and 90 min at RT then terminated with 6 µl 100 mM EDTA. 12 µL of 1.5 µM SA-XL and 3 nM PT66 in KF Buffer was added to detect phosphorylation. The 665 nm FRET emission and europium 620 nm emission signals were recorded after 2 hr on an Envision. A control containing no enzyme was also prepared as a negative control.

Example 3

Determination of Substrate BTK Vmax and Km Values $V_{max}$ and $K_m$ values of BTK were determined at saturating ATP concentration (25 µM). Serial dilutions of BTK, starting at 12 µM, were prepared in 15 mM Hepes, pH 7.5 buffer containing 1% glycerol, 0.01% Tween 20, 1.875 mM DTT, and 1.875 mM MnCl₂. 37.5 nM EphB3 kinase was diluted in a 15 mM Hepes, pH 7.5 reaction buffer containing 1% glycerol, 0.01% Tween 20, 1.875 mM DTT, 1.875 mM MnCl₂, and 75 µM ATP. 2 µl of enzyme/ATP was incubated in a 384-well reaction plate with 1 µl of 1% DMSO in Hepes buffer, pH 7.5 for 30 min at RT. The enzyme reaction was initiated with 3 µl of BTK where the final reaction concentrations were 12.5 nM EphB3, 25 µM ATP, 1.875 mM MnCl2, and 0.33% DMSO with 6 µM or less BTK. Reactions were run for 30 min at RT then terminated with 6 µl 100 mM EDTA. 12 µL of SA-XL at 1:4 SA:B and 3 nM PT66 in Hepes KF buffer was added to detect phosphorylation. The 665 nm FRET emission and europium 620 nm emission signals were recorded after 2 hr on an Envision.

Example 4

Determination of ATP $V_{max}$ and $K_m$ Values $V_{max}$ and $K_m$ values of ATP were determined at saturating BTK concentration (6 µM). Serial dilutions of ATP, starting at 75 µM, were prepared in 15 mM Hepes, pH 7.5 buffer containing, 1% glycerol, 0.01% Tween 20, 1.875 mM DTT, 1.875 mM MnCl₂, and 37.5 nM EphB3. 12 µM BTK was diluted in a 15 mM Hepes, pH 7.5 reaction buffer containing 1% glycerol, 0.01% Tween 20, 1.875 mM DTT, and 1.875 mM MnCl₂. 2 µl of enzyme/ATP was incubated in 384-well reaction plate with 1 µl of 1% DMSO in Hepes buffer, pH 7.5 for 30 min at RT. The enzyme reaction was initiated with 3 µl of BTK where the final reaction concentrations were 12.5 nM EphB3, 6 µM BTK, 1.875 mM MnCl2, and 0.33% DMSO with 25 µM or less ATP. Reactions were run for 30 min at RT then terminated with 6 µl 100 mM EDTA. 12 µl of 1.5 µSA-XL and 3 nM PT66 in Hepes KF buffer were added to detect phosphorylation. The 665 nm FRET emission and europium 620 nm emission signals were recorded after 2 hr on an Envision.

Example 5

Enzyme Stability for Compound Testing and DMSO Tolerance

Figure 3:
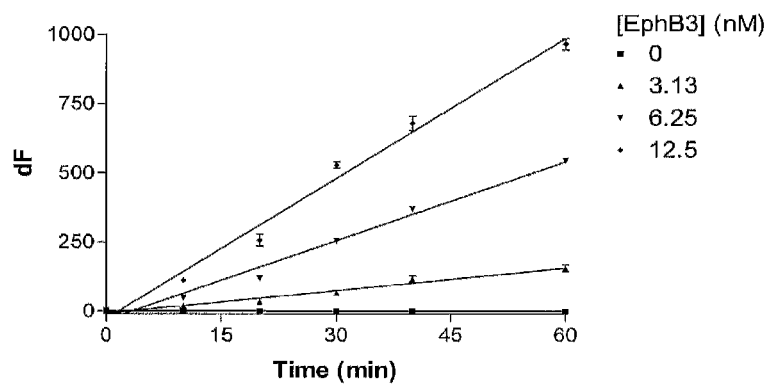
FIG. 3 is a graph relating to the determination of initial enzyme velocity and working concentration.

Enzyme activity is required to be stable in order to conduct high throughput screening and stability of the activity was excellent up to 60 min once we made the addition of 1.8 mM DTT to 15 mM Hepes buffer containing 1% glycerol, 0.01% Tween 20, and 1% DMSO (FIG. 3A). The metal ion dependency was examined and found that the enzyme activity was dependent on MnCl2. Phosphorylation was not detectable if MgCl2 was substituted for the MnCl2 (FIG. 3B). The highest level of enzyme activity was obtained with 1.25 mM MnCl2 (data not shown). Our small molecule library is made up in 100% DMSO which is then diluted in buffer for screening so it was important to establish the DMSO tolerance for the enzyme. EphB3 activity was tested in different final concentrations of DMSO and found to be slightly diminished with DMSO concentrations of 4% but less affected by concentrations less than 1% (FIG. 3A). EphB3 was tolerant to one freeze/thaw cycle and no significant differences in activity were observed between aliquots (FIG. 3D).

Example 6

Optimization of Enzyme Concentration and Km Determination

Figure 4A:
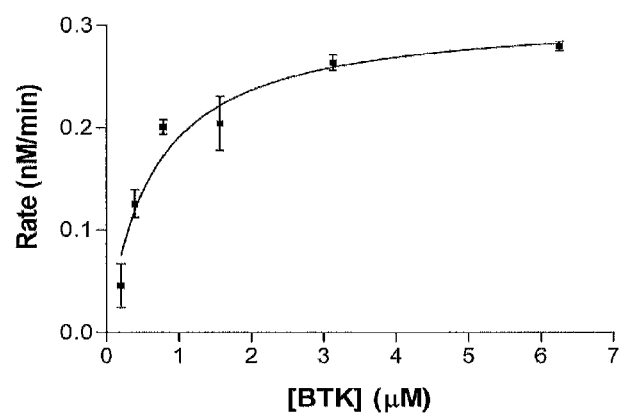
FIGS. 4A and 4B are graphs relating to $V_{max}$ and $K_m$ Determinations of BTK and ATP.
Figure 4B:
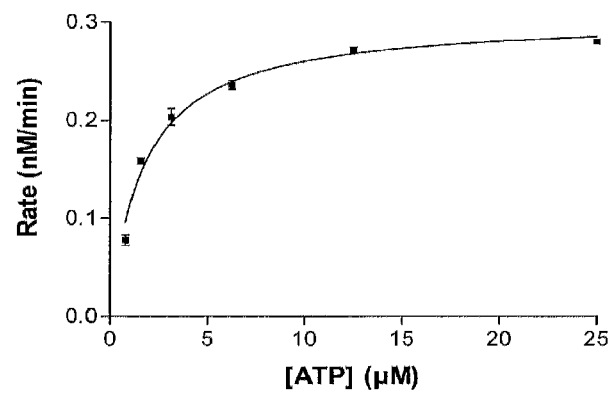

For compound testing, it is desirable to screen at enzyme concentrations that give a linear dependency with respect to time. At enzyme concentrations of 3.13, 6.25, and 12.5 nM progress curves were generated demonstrating linear kinetics for at least one hour (FIG. 3). 12.5 nM was chosen as the working concentration to determine the apparent Km of ATP and the BTK substrate. Compounds were screened at the Km concentrations for the BTK substrate and ATP to provide an assay that is sensitive to discover ATP competitive, uncompetitive, and non-competitive inhibitors. Initially, to determine the Km for BTK 12.5 nM EphB3 kinase under saturating conditions of ATP (25 µM) was used (FIG. 4A). The Vmax of BTK was determined to be ~0.3 nM/min and the apparent Km was ~600 nM. At saturating BTK substrate concentrations, a concentration-dependent response was observed (FIG. 4B). The Vmax of ATP was determined to be ~0.3 nM/min and the apparent Km was 2.0 μM. Overall, kinetics of the reaction suggested the binding mechanism of EphB3 with ATP and BTK to be random.

Example 7

Methods for In Vivo Studies

The following methods were used in Examples 8 and 9. Sprague-Dawley rats (Charles River Labs, NC), weighing 225-250 grams each were given free access to food and water before the experiment. For the induction of ischemia, the animals were anesthetized with halothane (1% in 70%/30% $NO_2/O_2$ by mask). Monitoring of mean arterial blood pressure (MABP) via tail cuff apparatus, and blood samples were collected to determine arterial pH levels and $PaCO_2$ and $PaO_2$. The MABP and heart rate were recorded using a Visitech System blood pressure monitor. Brain temperature was monitored using a rectal thermometer and thermistor probe inserted into the temporalis muscle. The animals' body temperature was maintained at 37° C. by using a water-jacketed heating pad. Brain temperature was monitored for 1 hour prior to ischemia to 6 hours following ischemia and recorded at 30-minute intervals. Each rat was anesthetized and the external carotid artery (ECA) and common carotid artery (CCA) isolated. The left common carotid artery (CCA) was exposed through a midline incision in the neck. The superior thyroid and occipital arteries was electrocoagulated and divided. A microsurgical clip was placed around the origin of the external carotid artery (ECA). The distal end of the ECA was ligated with 6-0 silk and transected. A 6-0 silk was tied loosely around the ECA stump. The clip was removed and the fire-polished tip of a 5-0 nylon suture (silicone coated) was gently inserted into the ECA stump. The loop of the 6-0 silk was tightened around the stump and the nylon suture was advanced approximately 13 mm (adjusted for body weight) into and through the internal carotid artery (ICA) until it rested in the anterior cerebral artery (ACA), thereby occluding the anterior communicating and middle cerebral arteries. After the nylon suture was in place for 2 hours, it was pulled back into the ECA and the incision closed.

At the end of the ischemic injury, animals were injected with compounds ICV through an opening (0.7 mm posterior to the bregma, 1.5 mm lateral to the midline, 5 mm ventral from the cranium). Under general anesthesia, an incision was made in the skin of the skull and the skin retracted and a small hole was made with a hand-held drill. The skull was cooled with water during drilling to reduce injury to the brain. Compounds were injected with a Hamilton syringe (over a 2 hour period depending upon volume). After injection the opening was closed with foil and plasticine and fixed with dental cement. The skin was closed with surgical staples.

For histological examination, the animals were anesthetized, the brains were transcardially perfused with 4° C., 10% phosphate-buffered saline (PBS), and the brains were removed and chilled for 15 minutes at −20° C. before being placed in a Rodent Brain Matrix. Coronal sections (1-mm thickness) were prepared and subjected to 2% triphenyltetrazolium chloride (TTC) staining at 37° C. Seven serial one-mm thick coronal sections through the rostral to caudal extent of the infarction were obtained from each brain, beginning two-mm from the frontal pole. The TTC stained sections were fixed in 10% neutral buffered formalin and kept in darkness at 4° C. for at least 24 hours. The infarct area in each section was determined with a computer-assisted image analysis system, consisting of a Power Macintosh computer equipped with a Quick Capture frame grabber card, Hitachi CCD camera mounted on an Olympus microscope and camera stand. NIH Image Analysis Software, v. 1.55 was used. The total area of damage was determined over the seven sections. A single operator blinded to treatment status performed all measurements. The infarct volume was calculated by summing the infarct volumes of the sections. Infarct size (%) was calculated by using the following formula: (contralateral volume−ipsilateral undamaged volume)×100/contralateral volume to eliminate effects of oedema.

Cerebral blood flow (CBF) was monitored by using a laser Doppler flowmeter. The CBF values were determined as a percentage, because the values displayed by the laser Doppler flowmeter were not absolute. As described above, the animals were anesthetized with halothane (1% in 70%/30% $NO_2/O_2$ by mask). CBF was compared at 15 minutes prior to the onset of ischemia, during ischemia (15 minutes after the start of ischemia) before injection of compound and at 30 minutes post injection (continuous measurements will be taken from 15 minutes prior to ischemia to 30 minutes after the end of injection of the compound and recorded every 30 minutes). The mean values before MCA occlusion was taken as baseline and the data thereafter expressed as percentages of the baseline value.

Behavioral analysis (neurological deficit) was determined in the rats before and after ischemic injury. Neurological scores were as follows: 0, normal motor function; 1, flexion of torso and contralateral forelimb when animal will be lifted by the tail; 2, circling to the contralateral side when held by tail on flat surface, but normal posture at rest; 3, leaning to the contralateral side at rest; 4, no spontaneous motor activity.

The results are expressed as the mean±standard deviation (SD). The significance of difference in the physiological and histological data was analyzed using a one-way analysis of variance (ANOVA) followed by Fisher's post hoc test. Repeated-measures ANOVA was computed on the monitoring data and the significance of the difference among groups will be evaluated by Fisher's post hoc test.

Example 8

Testing of Compound LDN-209926 (2099626 in Table 3 Above) in an Animal Model for Stroke Ischemia was produced in Sprague-Dawley rats by advancing a suture through the internal carotid artery (ICA) until it rested in the anterior cerebral artery (ACA) thereby occluding the anterior communicating and middle cerebral arteries. After two hours, the suture was pulled back and the incision was closed. After ischemia was induced, animals were injected with LDN-209926 ICV to look for protection.

Figure 6A:
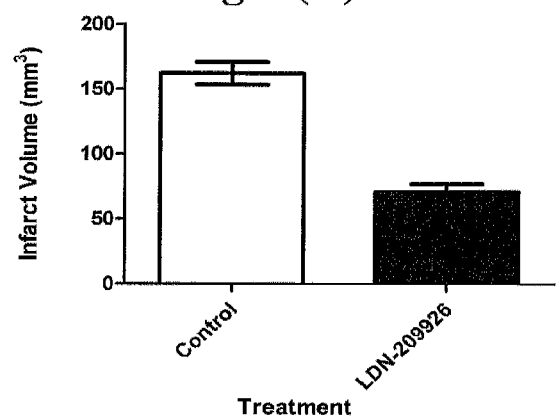
FIG. 6(A) depicts the effect of LDN-209926 on infarct volume as measured histologically from coronal sections stained with 2% triphenyltetrazolium chloride.

Infarct volume was measured histologically from coronal sections stained with 2% triphenyltetrazolium chloride (FIG. 6(A)). The infarct area was determined with a computer-assisted image analysis system from seven sections. The infarct volume was calculated by summing the infarct areas of the sections. Infarct size (%) was calculated by using the following formula: (contralateral volume−ipsilateral undamaged volume)×100/contralateral volume to eliminate effects of edema. Infarct volume was significantly reduced by LDN-209926 (FIG. 6(A)).

Figure 6B:
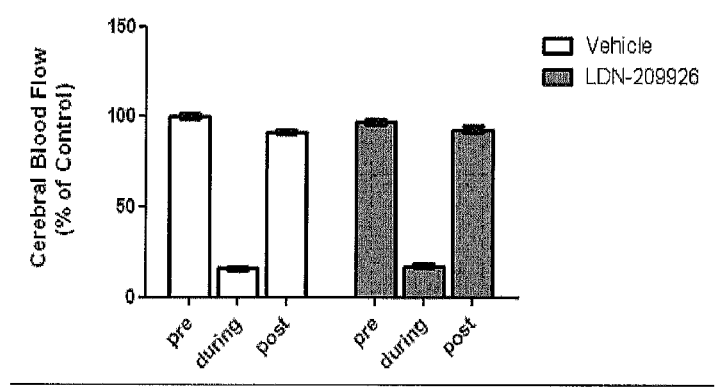
FIG. 6(B) depicts cerebral blood flow measured using a laser Doppler flowmeter pre-ischemia, during, and post-ischemia (vehicle v. LDN-209926).
Figure 6C:
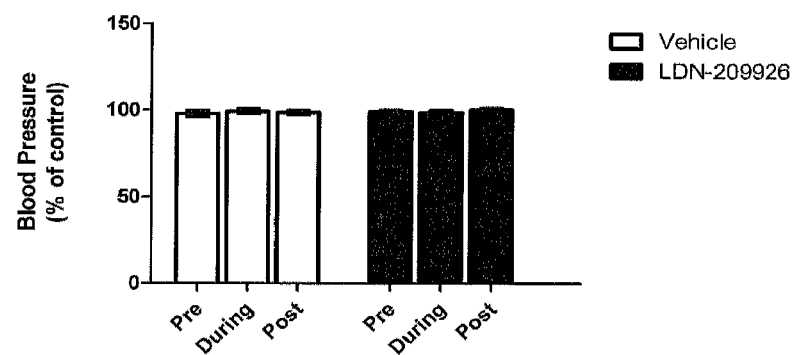
FIG. 6(C) depicts mean arterial blood pressure (MABP) measured via tail cuff apparatus and recorded using a Visitech System blood pressure monitor before, during or after ischemia (vehicle v. LDN-209926).

Cerebral blood flow was measured using a laser Doppler flowmeter pre-ischemia, during, and post-ischemia (FIG. 6(B)). LDN-209926 had no effect on blood flow. Mean arterial blood pressure (MABP) was measured via tail cuff apparatus and recorded using a Visitech System blood pressure monitor (FIG. 6(C)). Compound LDN-209926 had no effect on blood pressure before, during or after ischemia.

Figure 6D:
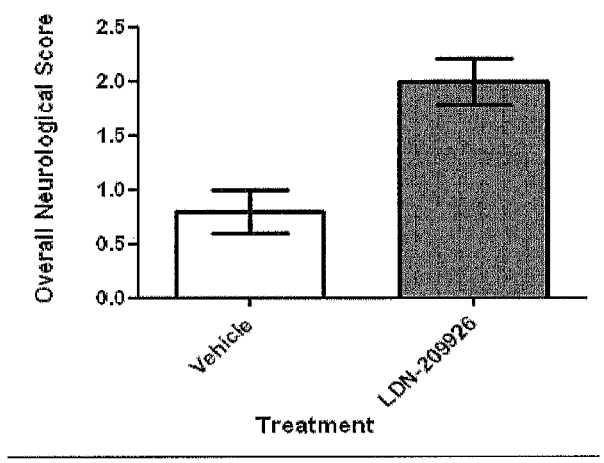
FIG. 6(D) depicts neurological score after compound LDN-209926 or vehicle treatment (rated between 0 (worst) and 4 (unaffected)).

Neurological score after compound or vehicle treatment was rated between 0 (worst) and 4 (unaffected). Treatment with LDN-209926 resulted in an improved neurological score (FIG. 6(D)).

Figure 6E:
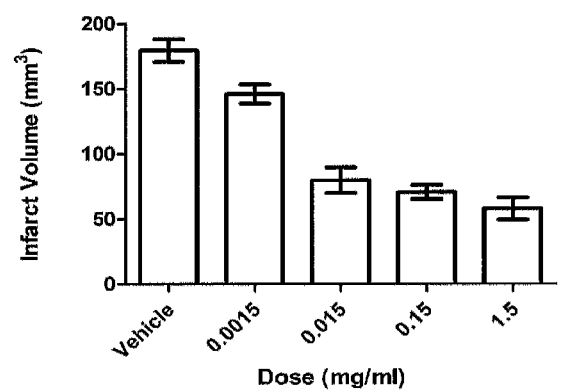
FIG. 6(E) depicts infarct volume measured at different compound doses of LDN-209926 administered ICV.
Figure 6F:
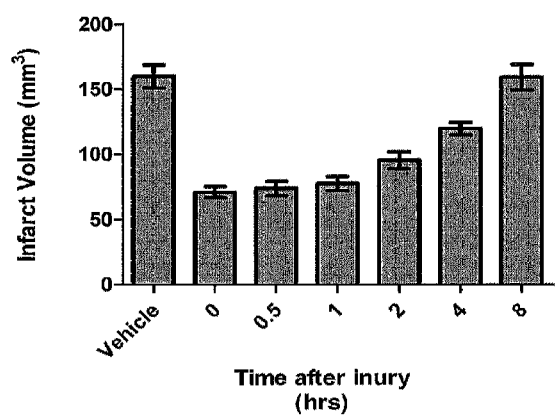
FIG. 6(F) depicts infarct volume measured after different times (0-8 hours) after ischemia, showing neuroprotective effect of LDN-209926 even when compound was administered four hours after ischemia.

Infarct volume was measured at different compound doses administered ICV. LDN-209926 gave a dose-dependent decrease in infarct volume (FIG. 6(E)). Infarct volume was measured after different times (0-8 hours) after ischemia. LDN-209926 was neuroprotective even when compound was administered four hours after ischemia (FIG. 6(F)).

Example 9

Figure 7A:
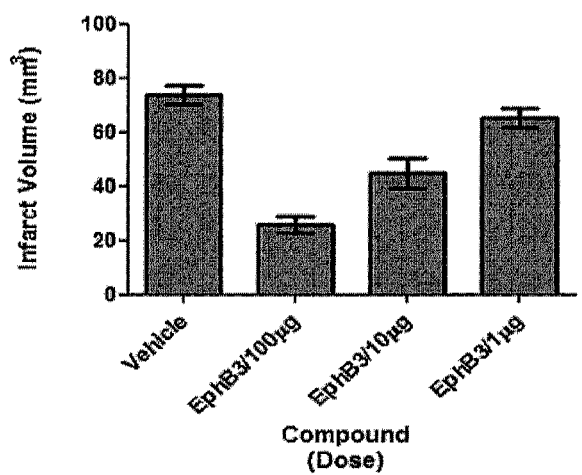
FIG. 7(A) depicts infarct volume measured at different compound doses of LDN-211904 administered ICV.
Figure 7B:
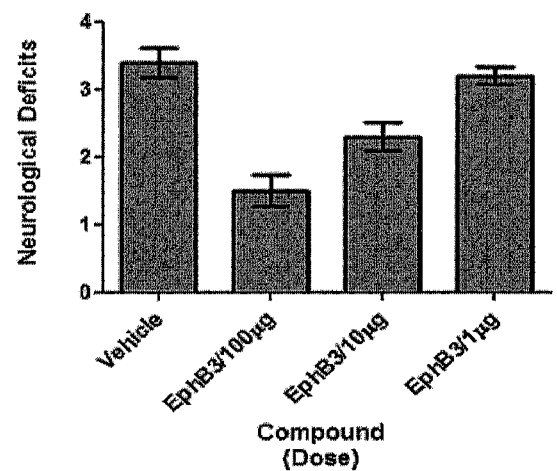
FIG. 7(B) depicts neurological deficit after compound LDN-211904 or vehicle treatment (rated between 0 (unaffected) and 4 (worst)).
Figure 8A:
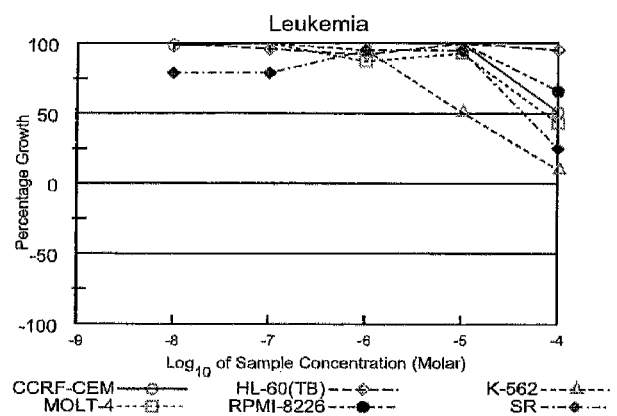
FIG. 8(A)-(I) depict dose-response curves for LDN-211904 against a panel of tumor cell lines (e.g., leukemia (A), non-small cell lung cancer (B), colon cancer (C), CNS cancer (D), melanoma (E), ovarian cancer (F), renal cancer (G), prostate cancer (H), and breast cancer (I).
Figure 8B:
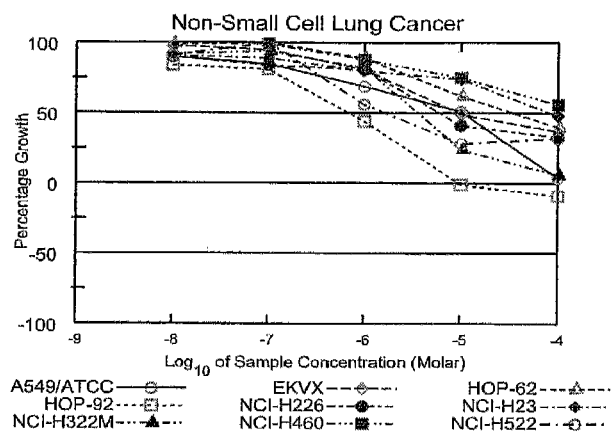
Figure 8C:
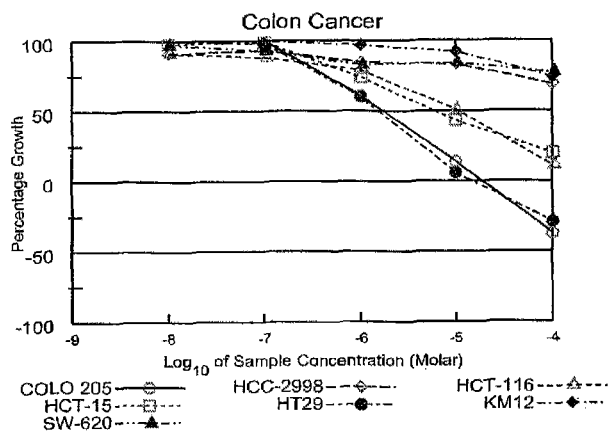
Figure 8D:
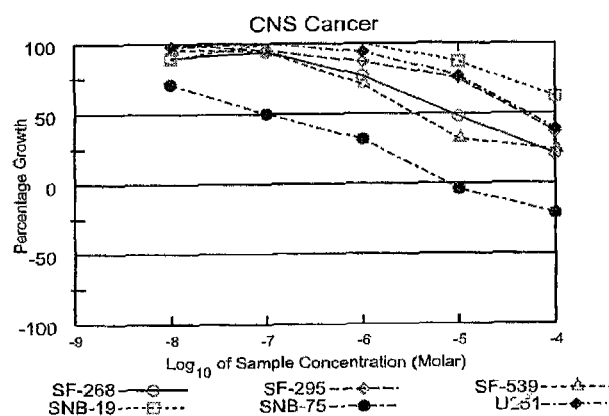
Figure 8E:
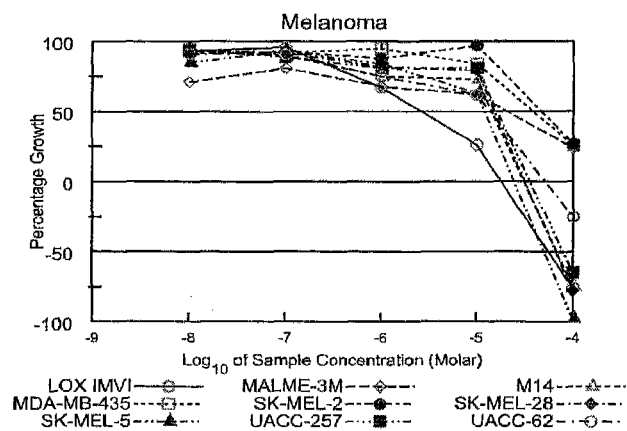
Figure 8F:
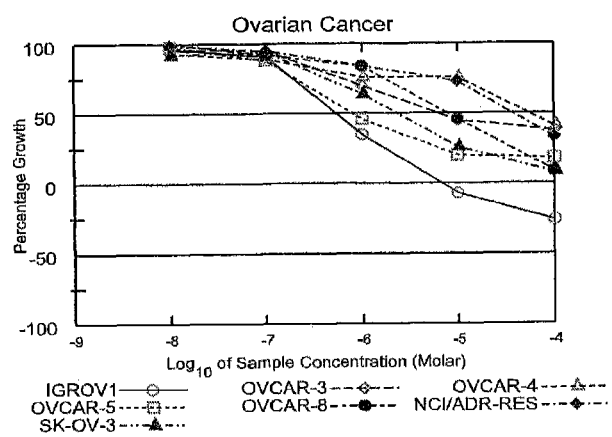
Figure 8G:
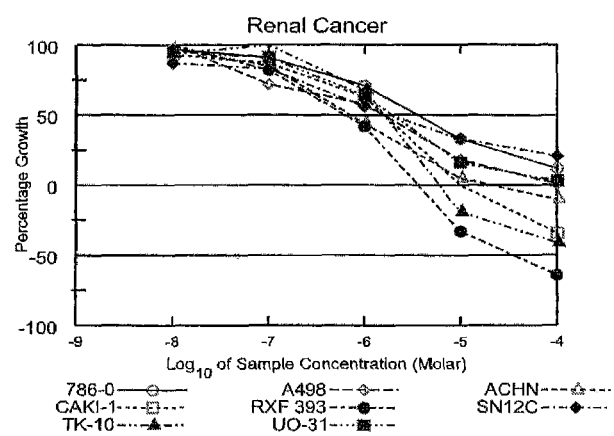
Figure 8H:
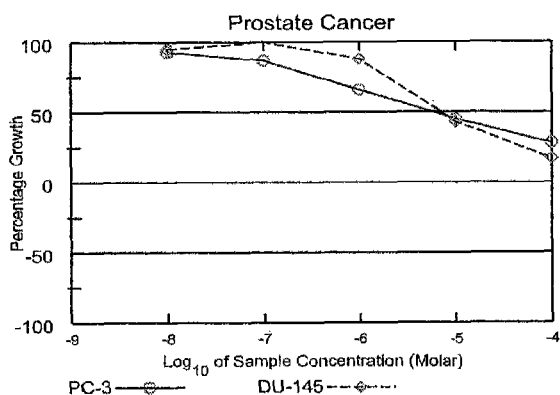
Figure 8I:
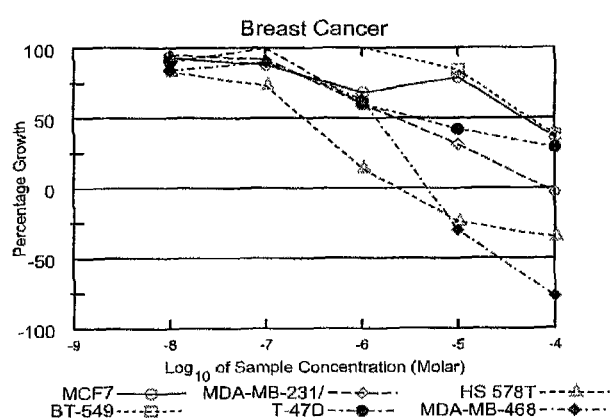

Testing of Compound LDN-211904 (211904 in Table 3 Above) in an Animal Model for Stroke Infarct volume was measured at different compound doses administered ICV. LDN-211904 showed dose-dependent decrease in infarct volume (FIG. 7(A)). Neurological deficit after compound or vehicle treatment was rated between 0 (unaffected) and 4 (worst). Treatment with LDN-211904 showed a dose-dependent neuroprotection in behavior (FIG. 7(B)).

Example 10

Dose-Response Effect of LDN-211904 Against a Panel of Tumor Cell Lines

Dose-response curves for LDN-211904 (211904 from Table 3 above) against a panel of tumor cell lines are shown in FIGS. 8(A)-(I). The y-axis depicts the % growth and the x-axis depicts the compound concentration. The legends below each graph refer to the different tumor cell lines used. In general, FIG. 8(A)-(I) demonstrate that growth of a variety of cell lines from different tumor types are inhibited by compound LDN-211904. The results were obtained by methods analogous to those below.

The human tumor cell lines of the cancer screening panel were grown in RPMI 1640 medium containing 5% fetal bovine serum and 2 mM L-glutamine. For a typical screening experiment, cells were inoculated into 96 well microtiter plates in 100 µL at plating densities ranging from 5,000 to 40,000 cells/well depending on the doubling time of individual cell lines. After cell inoculation, the microtiter plates were incubated at 37° C., 5% CO2, 95% air and 100% relative humidity for 24 hours prior to addition of experimental drugs.

After 24 hours, two plates of each cell line were fixed in situ with TCA, to represent a measurement of the cell population for each cell line at the time of drug addition (Tz). Experimental drugs were solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 µg/ml gentamicin. Additional four, 10-fold or ½ log serial dilutions were made to provide a total of five drug concentrations plus control. Aliquots of 100 µl of these different drug dilutions were added to the appropriate microtiter wells already containing 100 µl of medium, resulting in the required final drug concentrations.

Following drug addition, the plates were incubated for an additional 48 h at 37° C., 5% CO2, 95% air, and 100% relative humidity. For adherent cells, the assay was terminated by the addition of cold TCA. Cells were fixed in situ by the gentle addition of 50 µl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 µl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance is read on an automated plate reader at a wavelength of 515 nm. For suspension cells, the methodology was the same except that the assay was terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth was calculated at each of the drug concentrations levels. Percentage growth inhibition was calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters were calculated for each experimental agent. Growth inhibition of 50% (GI50) was calculated from $[(Ti-Tz)/(C-Tz)] \times 100 = 50$, which is the drug concentration resulting in a 50% reduction in the net protein increase (as measured by SRB staining) in control cells during the drug incubation. The drug concentration resulting in total growth inhibition (TGI) was calculated from Ti=Tz. The $LC_{50}$ (concentration of drug resulting in a 50% reduction in the measured protein at the end of the drug treatment as compared to that at the beginning) indicating a net loss of cells following treatment was calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A pharmaceutical composition comprising a compound of formula (II):

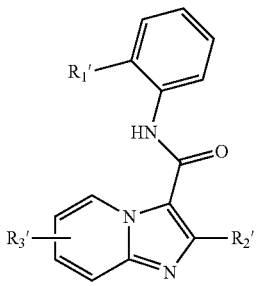

(II)

or a pharmaceutically acceptable salt thereof; wherein:
$R_1'$ is halogen;
$R_2'$ is selected from the group consisting of hydrogen and lower ($C_1$-$C_8$) alkyl; and
$R_3'$ is hydrogen, halogen, cycloalkyl, cycloheteroalkyl, aryl, or heteroaryl.

2. The composition of claim 1, wherein the compound is a compound of formula:

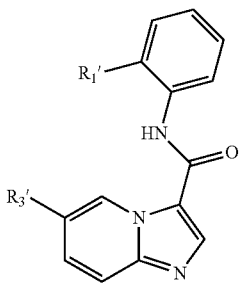

or a pharmaceutically acceptable salt thereof.

3. The composition of claim 2, wherein:
$R_1'$ is halogen; and
$R_3'$ is selected from the group consisting of hydrogen, halogen, cycloheteroalkyl and aryl.

4. The composition of claim 3, wherein $R_3'$ is selected from the group consisting of hydrogen, chlorine, phenyl, 4-chlorophenyl, 1-piperidinyl, 4-piperidinyl, and 4-piperidin-4-olyl.

5. The composition of claim 1, wherein the compound is selected from the group consisting of:
a. 6-bromo-N-(2-chlorophenyl)imidazo[1,2-a]pyridine-3-carboxamide;
b. N-(2-chlorophenyl)-6-phenylimidazo[1,2-a]pyridine-3-carboxamide;
c. N-(2-chlorophenyl)-6-(4-chlorophenyl)imidazo[1,2-a]pyridine-3-carboxamide;
e. N-(2-chlorophenyl)-2-methyl-6-phenylimidazo[1,2-a]pyridine-3-carboxamide;
f. N-(2-chlorophenyl)-6-(piperidin-4-yl)imidazo[1,2-a]pyridine-3-carboxamide; and
g. N-(2-chlorophenyl)-6-(4-hydroxypiperidin-4-yl)imidazo[1,2-a]pyridine-3-carboxamide;
or a pharmaceutically acceptable salt of any of the aforementioned.

6. A method of treating cancer or a neuronal system injury characterized by EphB3 kinase activity, the method comprising administering to a subject a therapeutically effective amount of an EphB3 kinase inhibitor compound to mitigate the medical condition, the EphB3 kinase inhibitor compound being selected from the group consisting of the composition of claim 1.

7. The method of claim 6, wherein said method is a method of treating cancer.

8. The method of claim 7, wherein said cancer is selected from the group consisting of leukemia, non-small cell lung cancer, colon cancer, CNS cancer, melanoma, ovarian cancer, renal cancer, prostate cancer, and breast cancer.

9. The method of claim 6, wherein said method is a method of treating a neuronal system injury.

10. The method of claim 9, wherein the neuronal system injury is a central nervous system injury selected from the group consisting of cerebral ischemia and traumatic brain injury.

11. The method of claim 6, wherein:
$R_1'$ is chlorine; and
$R_3'$ is selected from the group consisting of hydrogen, halogen, cycloheteroalkyl and aryl.

12. The method of claim 11, wherein $R_3'$ is selected from the group consisting of hydrogen, chlorine, phenyl, 4-chlorophenyl, 1-piperidinyl, 4-piperidinyl, and 4-piperidin-4-olyl.

13. The method of claim 6, wherein the compound is selected from the group consisting of:
6-bromo-N-(2-chlorophenyl)imidazo[1,2-a]pyridine-3-carboxamide;
N-(2-chlorophenyl)-6-phenylimidazo[1,2-a]pyridine-3-carboxamide;
N-(2-chlorophenyl)-6-(4-chlorophenyl)imidazo[1,2-a]pyridine-3-carboxamide;
N-(2-chlorophenyl)-2-methyl-6-phenylimidazo[1,2-a]pyridine-3-carboxamide;
N-(2-chlorophenyl)-6-(piperidin-4-yl)imidazo[1,2-a]pyridine-3-carboxamide; and
N-(2-chlorophenyl)-6-(4-hydroxypiperidin-4-yl)imidazo[1,2-a]pyridine-3-carboxamide;
or a pharmaceutically acceptable salt of any of the aforementioned.

14. The composition of claim 1, wherein $R_3'$ is cycloheteroalkyl or aryl.

15. The method of claim 6, wherein $R_3'$ is cycloheteroalkyl or aryl.

* * * * *

SEQUENCE LISTING

```
<160> NUMBER OF SEQ ID NOS: 4

<210> SEQ ID NO 1
<211> LENGTH: 998
<212> TYPE: PRT
<213> ORGANISM: Homo sapiens
```

<400> SEQUENCE: 1

```
Met Ala Arg Ala Arg Pro Pro Pro Ser Pro Pro Gly Leu
  1               5                  10                 15

Leu Pro Leu Leu Pro Pro Leu Leu Leu Pro Leu Leu Leu Pro
              20                  25                  30

Ala Gly Cys Arg Ala Leu Glu Glu Thr Leu Met Asp Thr Lys Trp Val
              35                  40                  45

Thr Ser Glu Leu Ala Trp Thr Ser His Pro Glu Ser Gly Trp Glu Glu
 50                  55                  60

Val Ser Gly Tyr Asp Glu Ala Met Asn Pro Ile Arg Thr Tyr Gln Val
 65                  70                  75                  80

Cys Asn Val Arg Glu Ser Ser Gln Asn Asn Trp Leu Arg Thr Gly Phe
                  85                  90                  95

Ile Trp Arg Arg Asp Val Gln Arg Val Tyr Val Glu Leu Lys Phe Thr
                 100                 105                 110

Val Arg Asp Cys Asn Ser Ile Pro Asn Ile Pro Gly Ser Cys Lys Glu
                 115                 120                 125

Thr Phe Asn Leu Phe Tyr Tyr Glu Ala Asp Ser Asp Val Ala Ser Ala
     130                 135                 140

Ser Ser Pro Phe Trp Met Glu Asn Pro Tyr Val Lys Val Asp Thr Ile
145                 150                 155                 160

Ala Pro Asp Glu Ser Phe Ser Arg Leu Asp Ala Gly Arg Val Asn Thr
                 165                 170                 175

Lys Val Arg Ser Phe Gly Pro Leu Ser Lys Ala Gly Phe Tyr Leu Ala
                 180                 185                 190

Phe Gln Asp Gln Gly Ala Cys Met Ser Leu Ile Ser Val Arg Ala Phe
     195                 200                 205

Tyr Lys Lys Cys Ala Ser Thr Thr Ala Gly Phe Ala Leu Phe Pro Glu
210                 215                 220

Thr Leu Thr Gly Ala Glu Pro Thr Ser Leu Val Ile Ala Pro Gly Thr
225                 230                 235                 240

Cys Ile Pro Asn Ala Val Glu Val Ser Val Pro Leu Lys Leu Tyr Cys
                 245                 250                 255

Asn Gly Asp Gly Glu Trp Met Val Pro Val Gly Ala Cys Thr Cys Ala
                 260                 265                 270

Thr Gly His Glu Pro Ala Ala Lys Glu Ser Gln Cys Arg Pro Cys Pro
     275                 280                 285

Pro Gly Ser Tyr Lys Ala Lys Gln Gly Glu Gly Pro Cys Leu Pro Cys
     290                 295                 300

Pro Pro Asn Ser Arg Thr Thr Ser Pro Ala Ala Ser Ile Cys Thr Cys
305                 310                 315                 320

His Asn Asn Phe Tyr Arg Ala Asp Ser Asp Ser Ala Asp Ser Ala Cys
                 325                 330                 335

Thr Thr Val Pro Ser Pro Arg Gly Val Ile Ser Asn Val Asn Glu
                 340                 345                 350

Thr Ser Leu Ile Leu Glu Trp Ser Glu Pro Arg Asp Leu Gly Gly Arg
     355                 360                 365

Asp Asp Leu Leu Tyr Asn Val Ile Cys Lys Lys Cys His Gly Ala Gly
     370                 375                 380

Gly Ala Ser Ala Cys Ser Arg Cys Asp Asp Asn Val Glu Phe Val Pro
385                 390                 395                 400

Arg Gln Leu Gly Leu Thr Glu Arg Arg Val His Ile Ser His Leu Leu
                 405                 410                 415
```

-continued

```
Ala His Thr Arg Tyr Thr Phe Glu Val Gln Ala Val Asn Gly Val Ser
            420                 425                 430
Gly Lys Ser Pro Leu Pro Pro Arg Tyr Ala Ala Val Asn Ile Thr Thr
        435                 440                 445
Asn Gln Ala Ala Pro Ser Glu Val Pro Thr Leu Arg Leu His Ser Ser
    450                 455                 460
Ser Gly Ser Ser Leu Thr Leu Ser Trp Ala Pro Pro Glu Arg Pro Asn
465                 470                 475                 480
Gly Val Ile Leu Asp Tyr Glu Met Lys Tyr Phe Glu Lys Ser Glu Gly
                485                 490                 495
Ile Ala Ser Thr Val Thr Ser Gln Met Asn Ser Val Gln Leu Asp Gly
            500                 505                 510
Leu Arg Pro Asp Ala Arg Tyr Val Val Gln Val Arg Ala Arg Thr Val
        515                 520                 525
Ala Gly Tyr Gly Gln Tyr Ser Arg Pro Ala Glu Phe Glu Thr Thr Ser
    530                 535                 540
Glu Arg Gly Ser Gly Ala Gln Gln Leu Gln Glu Gln Leu Pro Leu Ile
545                 550                 555                 560
Val Gly Ser Ala Thr Ala Gly Leu Val Phe Val Ala Val Val Val Val
                565                 570                 575
Ile Ala Ile Val Cys Leu Arg Lys Gln Arg His Gly Ser Asp Ser Glu
            580                 585                 590
Tyr Thr Glu Lys Leu Gln Gln Tyr Ile Ala Pro Gly Met Lys Val Tyr
        595                 600                 605
Ile Asp Pro Phe Thr Tyr Glu Asp Pro Asn Glu Ala Val Arg Glu Phe
    610                 615                 620
Ala Lys Glu Ile Asp Val Ser Cys Val Lys Ile Glu Glu Val Ile Gly
625                 630                 635                 640
Ala Gly Glu Phe Gly Glu Val Cys Arg Gly Arg Leu Lys Gln Pro Gly
                645                 650                 655
Arg Arg Glu Val Phe Val Ala Ile Lys Thr Leu Lys Val Gly Tyr Thr
            660                 665                 670
Glu Arg Gln Arg Arg Asp Phe Leu Ser Glu Ala Ser Ile Met Gly Gln
        675                 680                 685
Phe Asp His Pro Asn Ile Ile Arg Leu Glu Gly Val Val Thr Lys Ser
    690                 695                 700
Arg Pro Val Met Ile Leu Thr Glu Phe Met Glu Asn Cys Ala Leu Asp
705                 710                 715                 720
Ser Phe Leu Arg Leu Asn Asp Gly Gln Phe Thr Val Ile Gln Leu Val
                725                 730                 735
Gly Met Leu Arg Gly Ile Ala Ala Gly Met Lys Tyr Leu Ser Glu Met
            740                 745                 750
Asn Tyr Val His Arg Asp Leu Ala Ala Arg Asn Ile Leu Val Asn Ser
        755                 760                 765
Asn Leu Val Cys Lys Val Ser Asp Phe Gly Leu Ser Arg Phe Leu Glu
    770                 775                 780
Asp Asp Pro Ser Asp Pro Thr Tyr Thr Ser Ser Leu Gly Gly Lys Ile
785                 790                 795                 800
Pro Ile Arg Trp Thr Ala Pro Glu Ala Ile Ala Tyr Arg Lys Phe Thr
                805                 810                 815
Ser Ala Ser Asp Val Trp Ser Tyr Gly Ile Val Met Trp Glu Val Met
            820                 825                 830
```

-continued

```
Ser Tyr Gly Glu Arg Pro Tyr Trp Asp Met Ser Asn Gln Asp Val Ile
        835                 840                 845

Asn Ala Val Glu Gln Asp Tyr Arg Leu Pro Pro Met Asp Cys Pro
850                 855                 860

Thr Ala Leu His Gln Leu Met Leu Asp Cys Trp Val Arg Asp Arg Asn
865                 870                 875                 880

Leu Arg Pro Lys Phe Ser Gln Ile Val Asn Thr Leu Asp Lys Leu Ile
                885                 890                 895

Arg Asn Ala Ala Ser Leu Lys Val Ile Ala Ser Ala Gln Ser Gly Met
                900                 905                 910

Ser Gln Pro Leu Leu Asp Arg Thr Val Pro Asp Tyr Thr Thr Phe Thr
        915                 920                 925

Thr Val Gly Asp Trp Leu Asp Ala Ile Lys Met Gly Arg Tyr Lys Glu
        930                 935                 940

Ser Phe Val Ser Ala Gly Phe Ala Ser Phe Asp Leu Val Ala Gln Met
945                 950                 955                 960

Thr Ala Glu Asp Leu Leu Arg Ile Gly Val Thr Leu Ala Gly His Gln
                965                 970                 975

Lys Lys Ile Leu Ser Ser Ile Gln Asp Met Arg Leu Gln Met Asn Gln
                980                 985                 990

Thr Leu Pro Val Gln Val
        995

<210> SEQ ID NO 2
<211> LENGTH: 350
<212> TYPE: PRT
<213> ORGANISM: Homo sapiens

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Gly Ser Gln Tyr Ile Ala
                20                  25                  30

Pro Gly Met Lys Val Tyr Ile Asp Pro Phe Thr Tyr Glu Asp Pro Asn
            35                  40                  45

Glu Ala Val Arg Glu Phe Ala Lys Glu Ile Asp Val Ser Cys Val Lys
50                  55                  60

Ile Glu Glu Val Ile Gly Ala Gly Glu Phe Gly Glu Val Cys Arg Gly
65                  70                  75                  80

Arg Leu Lys Gln Pro Gly Arg Arg Glu Val Phe Val Ala Ile Lys Thr
                85                  90                  95

Leu Lys Val Gly Tyr Thr Glu Arg Gln Arg Arg Asp Phe Leu Ser Glu
            100                 105                 110

Ala Ser Ile Met Gly Gln Phe Asp His Pro Asn Ile Ile Arg Leu Glu
            115                 120                 125

Gly Val Val Thr Lys Ser Arg Pro Val Met Ile Leu Thr Glu Phe Met
        130                 135                 140

Glu Asn Cys Ala Leu Asp Ser Phe Leu Arg Leu Asn Asp Gly Gln Phe
145                 150                 155                 160

Thr Val Ile Gln Leu Val Gly Met Leu Arg Gly Ile Ala Ala Gly Met
                165                 170                 175

Lys Tyr Leu Ser Glu Met Asn Tyr Val His Arg Asp Leu Ala Ala Arg
            180                 185                 190

Asn Ile Leu Val Asn Ser Asn Leu Val Cys Lys Val Ser Asp Phe Gly
        195                 200                 205
```

```
Leu Ser Arg Phe Leu Glu Asp Asp Pro Ser Asp Pro Thr Tyr Thr Ser
    210                 215                 220

Ser Leu Gly Gly Lys Ile Pro Ile Arg Trp Thr Ala Pro Glu Ala Ile
225                 230                 235                 240

Ala Tyr Arg Lys Phe Thr Ser Ala Ser Asp Val Trp Ser Tyr Gly Ile
                    245                 250                 255

Val Met Trp Glu Val Met Ser Tyr Gly Glu Arg Pro Tyr Trp Asp Met
                260                 265                 270

Ser Asn Gln Asp Val Ile Asn Ala Val Glu Gln Asp Tyr Arg Leu Pro
            275                 280                 285

Pro Pro Met Asp Cys Pro Thr Ala Leu His Gln Leu Met Leu Asp Cys
        290                 295                 300

Trp Val Arg Asp Arg Asn Leu Arg Pro Lys Phe Ser Gln Ile Val Asn
305                 310                 315                 320

Thr Leu Asp Lys Leu Ile Arg Asn Ala Ala Ser Leu Lys Val Ile Ala
                325                 330                 335

Ser Ala Gln Ser Gly Met Ser Gln Pro Leu Leu Asp Arg Thr
                340                 345                 350

<210> SEQ ID NO 3
<211> LENGTH: 541
<212> TYPE: PRT
<213> ORGANISM: Homo sapiens

<400> SEQUENCE: 3

Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

His Asn Gln Thr Ser Leu Tyr Lys Lys Ala Gly Ser Ala Ala Ala Pro
```

```
            225                 230                 235                 240

Phe Thr Glu Phe Ala Lys Glu Ile Asp Val Ser Cys Val Lys Ile Glu
                        245                 250                 255

Glu Val Ile Gly Ala Gly Glu Phe Gly Val Cys Arg Gly Arg Leu
                        260                 265                 270

Lys Gln Pro Gly Arg Arg Glu Val Phe Val Ala Ile Lys Thr Leu Lys
                        275                 280                 285

Val Gly Tyr Thr Glu Arg Gln Arg Arg Asp Phe Leu Ser Glu Ala Ser
                        290                 295                 300

Ile Met Gly Gln Phe Asp His Pro Asn Ile Ile Arg Leu Glu Gly Val
        305                 310                 315                 320

Val Thr Lys Ser Arg Pro Val Met Ile Leu Thr Glu Phe Met Glu Asn
                        325                 330                 335

Cys Ala Leu Asp Ser Phe Leu Arg Leu Asn Asp Gly Gln Phe Thr Val
                        340                 345                 350

Ile Gln Leu Val Gly Met Leu Arg Gly Ile Ala Ala Gly Met Lys Tyr
                        355                 360                 365

Leu Ser Glu Met Asn Tyr Val His Arg Asp Leu Ala Ala Arg Asn Ile
                        370                 375                 380

Leu Val Asn Ser Asn Leu Val Cys Lys Val Ser Asp Phe Gly Leu Ser
        385                 390                 395                 400

Arg Phe Leu Glu Asp Asp Pro Ser Asp Pro Thr Tyr Thr Ser Ser Leu
                        405                 410                 415

Gly Gly Lys Ile Pro Ile Arg Trp Thr Ala Pro Glu Ala Ile Ala Tyr
                        420                 425                 430

Arg Lys Phe Thr Ser Ala Ser Asp Val Trp Ser Tyr Gly Ile Val Met
                        435                 440                 445

Trp Glu Val Met Ser Tyr Gly Glu Arg Pro Tyr Trp Asp Met Ser Asn
                        450                 455                 460

Gln Asp Val Ile Asn Ala Val Glu Gln Asp Tyr Arg Leu Pro Pro Pro
        465                 470                 475                 480

Met Asp Cys Pro Thr Ala Leu His Gln Leu Met Leu Asp Cys Trp Val
                        485                 490                 495

Arg Asp Arg Asn Leu Arg Pro Lys Phe Ser Gln Ile Val Asn Thr Leu
                        500                 505                 510

Asp Lys Leu Ile Arg Asn Ala Ala Ser Leu Lys Val Ile Ala Ser Lys
                        515                 520                 525

Gly Gly Arg Ala Asp Pro Ala Phe Leu Tyr Lys Val Val
                        530                 535                 540

<210> SEQ ID NO 4
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: PHOSPHORYLATION
<222> LOCATION: 14
<223> OTHER INFORMATION: the site of phosphorylation

<400> SEQUENCE: 4

Ala Gly Ala Gly Leu Lys Lys Val Ala Leu Tyr Asp Tyr Met Pro
 1               5                  10                  15

Met
```